US008685962B2

(12) United States Patent
Gavish et al.

(10) Patent No.: US 8,685,962 B2
(45) Date of Patent: Apr. 1, 2014

(54) COMPOSITIONS, ARTICLES AND METHODS COMPRISING TSPO LIGANDS FOR PREVENTING OR REDUCING TOBACCO-ASSOCIATED DAMAGE

(75) Inventors: Moshe Gavish, Tel-Aviv (IL); Rafael M. Nagler, Timrat (IL)

(73) Assignee: Technion Research & Development Foundation Limited, Haifa (IL)

( * ) Notice: Subject to any disclaimer, the term of this patent is extended or adjusted under 35 U.S.C. 154(b) by 254 days.

(21) Appl. No.: 12/452,482

(22) PCT Filed: Jul. 2, 2008

(86) PCT No.: PCT/IL2008/000907
§ 371 (c)(1),
(2), (4) Date: Mar. 15, 2010

(87) PCT Pub. No.: WO2009/004621
PCT Pub. Date: Jan. 8, 2009

(65) Prior Publication Data
US 2010/0179133 A1 Jul. 15, 2010

Related U.S. Application Data

(60) Provisional application No. 60/929,546, filed on Jul. 2, 2007.

(51) Int. Cl.
| | | |
|---|---|---|
| *A01N 43/62* | (2006.01) | |
| *A61K 31/55* | (2006.01) | |
| *A01N 25/00* | (2006.01) | |
| *A61K 9/72* | (2006.01) | |
| *A61L 9/02* | (2006.01) | |
| *A61K 51/00* | (2006.01) | |
| *A61M 36/14* | (2006.01) | |

(52) U.S. Cl.
USPC ............. 514/221; 514/958; 424/40; 424/1.29

(58) Field of Classification Search
USPC ............................ 514/221, 958; 424/1.29, 40
See application file for complete search history.

(56) References Cited

U.S. PATENT DOCUMENTS

| | | | |
|---|---|---|---|
| 4,303,083 A | 12/1981 | Burruss, Jr. | |
| 5,099,861 A | 3/1992 | Clearman et al. | |
| 5,829,449 A * | 11/1998 | Hersh et al. ................. | 131/202 |
| 2004/0102440 A1* | 5/2004 | Wong .......................... | 514/238.8 |
| 2006/0074050 A1* | 4/2006 | Chang et al. ................ | 514/54 |

FOREIGN PATENT DOCUMENTS

| | | | |
|---|---|---|---|
| EP | 0358114 | | 3/1990 |
| IT | 2002MO0256MT | * | 9/2002 |
| WO | WO 01/70052 | | 9/2001 |
| WO | WO 2008/023357 | | 2/2008 |
| WO | WO 2009/004621 | | 1/2009 |

OTHER PUBLICATIONS

Park et al. (Cancer, Jun. 15, 2012, 3153-3164).*
Bel Marra Health (http://www.prweb.com/releases /2012/8/prweb9780007.htm).*
Baraldi (IT2002MO0256MT)—English translation, 2002.*
Communication Pursuant to Article 94(3) EPC Dated Aug. 10, 2011 From the European Patent Office Re. Application No. 08763663.5.
Carayon et al. "Involvement of Peripheral Benzodiazepine Receptors in the Protection of Hematopoietic Cells Against Oxygen Radical Damage", Blood, XP002091195, 87(8): 3170-3178, Apr. 15, 1996.
Leducq et al. "Role of Peripheral Benzodiazepine Receptors in Mitochondrial, Cellular, and Cardiac Damage Induced by Oxidative Stress and Ischemia-Reperfusion", Journal of Pharmacology and Experimental Therapeutics, XP002445342, 306(3): 828-837, Sep. 1, 2003. Abstract, P.830, Right Col., § 5, P.831, Table 1, Fig.1.
International Preliminary Report on Patentability Dated Jan. 14, 2010 From the International Bureau of WIPO Re.: Application No. PCT/IL2008/000907.
International Search Report Dated Nov. 10, 2008 From the International Searching Authority Re.: Application No. PCT/IL2008/000907.
Written Opinion Dated Nov. 10, 2008 From the International Searching Authority Re.: Application No. PCT/IL2008/000907.
Almirall et al. "Risk Factors for Communication-Acquired Pneumonia in Adults: A Population-Based Case-Control Study", European Respiratory Journal, XP002501020, 13(2): 349-355, Feb. 1999. Abstract, P.349, Right Col., § 1, Lines 3-5, P.350, Right Col., Last §, P.351, Right Col., § 1-2, P.352, Table 2, Left Col., § 1.
Branley et al. "Peripheral-Type Benzodiazepine Receptors in Bronchoalveolar Lavage Cells of Patients With Interstitial Lung Disease", Nuclear Medicine and Biology, XP022130617, 34(5): 553-558, Jun. 22, 2007. P.553, Abstract, Left Col., § 1, P.557, Left Col., § 2, Right Col., § 2.
Delpierre et al. "Influence of Anxiolytic Drugs (Prazepam and Diazepam) on Respiratory Center Output and CO2 Chemosensitivity in Patients With Lung Diseases", Respiration, XP009107573, 42(1): 15-20, Jan. 1, 1981. P.15, Abstract, P.16, Table 1.
Galiegue et al. "The Peripheral Benzodiazepine Receptor: A Promising Therapeutic Drug Target", Current Medicinal Chemistry, XP009027200, 10(16): 1563-1572, Jan. 1, 2003. Abstract, P.1563, Left Col., § 2, , Right Col., § 1, Fig.1, P.1565, Left Col., § 2, P.1570, Left Col., § 1.
Nagai et al. "Smoking-Related Interstitial Lung Diseases", Current Opinion in Pulmonary Medicine, XP009107630, 6(5): 415-419, Sep. 2000. P.425, Abstract, Right Col., § 2, P.416, Right Col., § 3, P.417, Right Col., § 4.
Pelaia et al. "Is the Mitochondrial Benzodiazepine Receptor Involved in the control of Airway Smooth Muscle Tone?", General Pharmacology, XP001127457, 28(4): 495-498, Jan. 1, 1997. Abstract, P.495, Right Col., § 3-5, P.496, Left Col., § 1-3, P.497, Left Col., § 4/5, Right Col., § 1-2, Last §.

(Continued)

*Primary Examiner* — Sreeni Padmanabhan
*Assistant Examiner* — Uma Ramachandran

(57) ABSTRACT

Articles of manufacturing (such as tobacco products), methods, devices and compositions for preventing or reducing tobacco-associated damage and/or disorders associated with oxidative stress in a subject, and which utilize a TSPO receptor ligand (such as diazepam), are disclosed.

16 Claims, 19 Drawing Sheets

(56) References Cited

OTHER PUBLICATIONS

Rahman et al. "Cigarette Smoke, Oxidative Stress and Corticosteroid Responsiveness", Chronic Obstructive Pulmonary Disease: Pathogenesis to Treatment: Novartis Foundation Symposium 234, XP002501072, 234(Chap.8): 125-144, 2001.

Communication Pursuant to Article 94(3) EPC Dated Jul. 16, 2013 From the European Patent Office Re. Application No. 08763663.5.
Leffingwell "Leaf Chemistry: Basic Chemical Constituents of Tobacco Leaf and Differences Among Tobacco Types", Tobacco: Production, Chemistry and Technology, XP055069386, Chap.8A: 265-284, 1999.

* cited by examiner

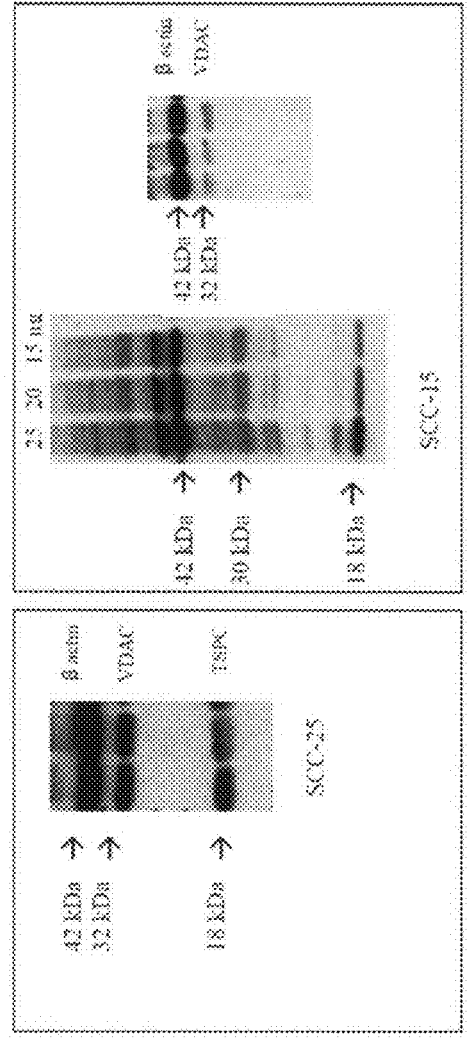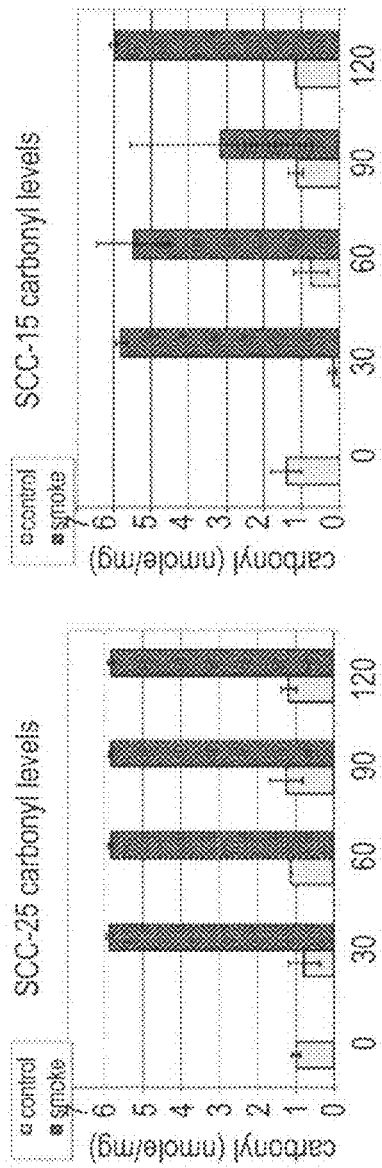

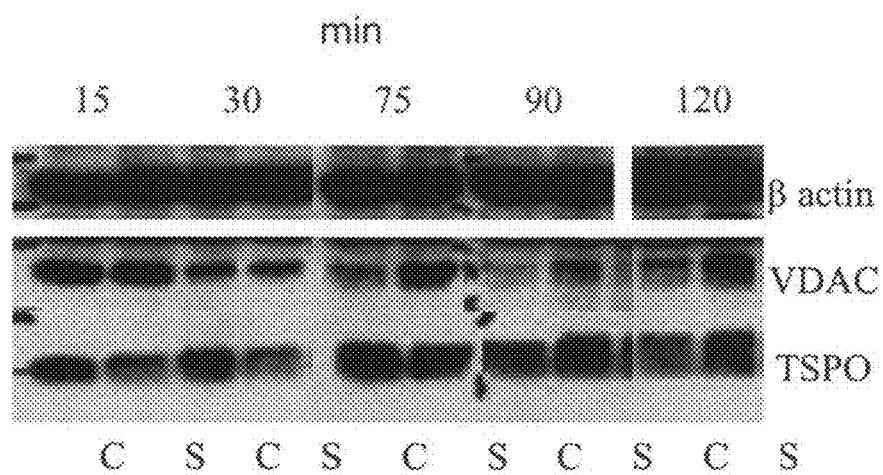
Fig. 12C
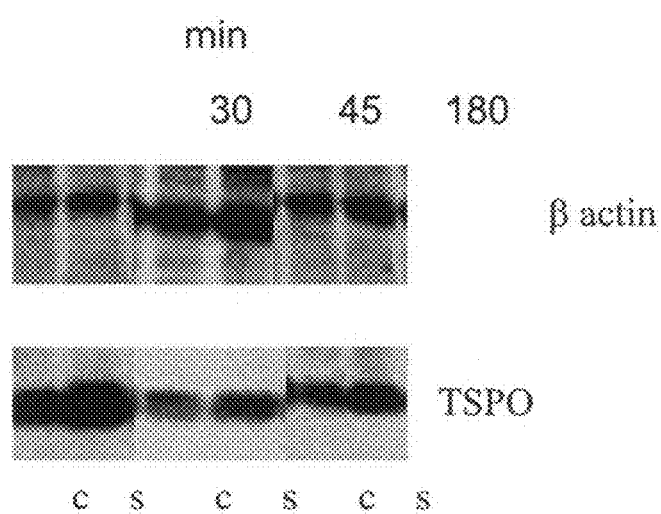
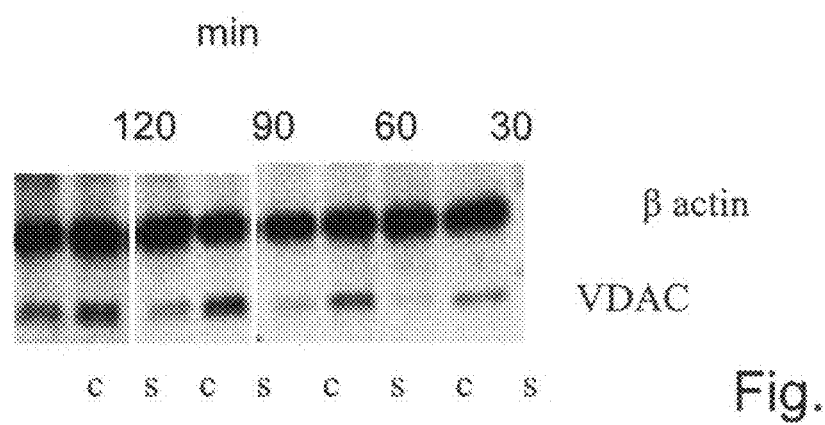
Fig. 12D

COMPOSITIONS, ARTICLES AND METHODS COMPRISING TSPO LIGANDS FOR PREVENTING OR REDUCING TOBACCO-ASSOCIATED DAMAGE

RELATED APPLICATIONS

This Application is a National Phase of PCT Patent Application No. PCT/IL2008/000907 having International filing date of Jul. 2, 2008, which claims the benefit of U.S. Provisional Patent Application No. 60/929,546 filed on Jul. 2, 2007. The contents of the above Applications are all incorporated herein by reference.

FIELD AND BACKGROUND OF THE INVENTION

The present invention, in some embodiments thereof, relates to articles, compositions and methods for reducing or preventing oxidative stress-associated cellular or macromolecular damage, such as tobacco-induced damage.

The deleterious effects of tobacco abuse are well known. Tobacco is a worldwide public health hazard accounting for significant morbidity and mortality. Although smoking places an abundant oxidant insult to the oropharynx and respiratory tract, the oxidant burden associated with any tobacco consumption (as described hereinbelow) is deleterious to the entire body of the tobacco consumer.

Tobacco consumption leads to development or enhancement of atherosclerosis, cardiovascular diseases, chronic obstructive pulmonary disease, lung cancer, as well as other forms of cancer and peripheral vascular diseases.

Cardiovascular disease is the main cause of death due to smoking. Cardiovascular disease can take many forms, depending on which blood vessels are involved. Main forms include coronary thrombosis, which may lead to a heart attack; cerebral thrombosis, which may lead to collapse, stroke and paralysis; affected kidney arteries, which result in high blood pressure or kidney failure; and blockage of the vascular supply to the legs, which may lead to gangrene and amputation.

Tobacco consumers are more likely to get cancer than non-smokers, particularly carcinomas of the mouth, pharynx, esophagus and lung. Other types of cancer associated with tobacco consumption include bladder cancer, cancer of the oesophagus, cancer of the kidneys, cancer of the pancreas and cervical cancer.

Chronic obstructive pulmonary disease (COPD) is a collective term for a group of conditions that involve block of airflow and include, for example: emphysema and chronic bronchitis.

Other risks associated with tobacco consumption include hypertension, fertility problems, severe asthma, retinoic disorders such as macular degeneration and cataracts, ulcers, periodontal diseases, impotence, Diabetes type 2, Back pain, skin ailments such as premature ageing and wrinkling, osteoporosis, earlier menopause, and damaged and/or weakened immune system.

There are two principal ways to consume tobacco: smoking and smoke-less consumption. The latter comes in various forms: snuff, snus and chewing tobacco. Snuff is a fine-grain tobacco that often comes in teabag-like pouches, which users "pinch" or "dip" between their lower lip and gum. Chewing tobacco comes in shredded, twisted, or "bricked" tobacco leaves that users put between their cheek and gum. Whether it is snuff, snus or chewing tobacco, the user consumes the tobacco letting it sit in the mouth and suck on the tobacco juices, spitting often to get rid of the saliva that builds up. This sucking and chewing allows nicotine (a narcotic drug), to be absorbed into the bloodstream through the tissues of the mouth. Smokeless tobacco has a detrimental effect on the oral cavity plus systemic effects from buccal absorption of nicotine and other chemicals.

Evidence shows that cigars as well as cigarettes are highly toxic and addictive. Tobacco smokers have a similar increased risk for oral and laryngeal cancers. Evidence indicates that one cigar generates levels of carcinogenic particles exceeding those generated by three cigarettes. Fumes from cigars are also of greater consequence to secondary smokers. Epidemiologic studies reveal greater frequencies of heart disease, emphysema, and cancers of the mouth and pharynx in cigar smokers when compared to matched non-smokers.

Tobacco, whether smoked or chewed, causes common untoward effects in the oral cavity. Tobacco smoke (TS) has two chances to exert its deleterious effects in the mouth; when it is inhaled by the smoker and on its exit during exhalation.

Over 30,000 new cases of cancer of the oral cavity are diagnosed annually, accounting for 2-4 percents of all new cancers. The great majority of these patients are users of tobacco products.

Oral squamous cell carcinoma (SCC) is the most common malignancy of the head and neck with a worldwide incidence of over 300,000 new cases annually. The disease is characterized by a high rate of morbidity and mortality (approximately 50%) and in this respect is similar to malignant melanoma. The major inducer of oral SCC is exposure to tobacco which is considered to be responsible for 50-90% of cases world-wide [Epstein and Scully, *SCD Special Care in Dentistry* 1997; 17:120-8; Holleb et al. *Textbook of Clinical Oncology*. The American Cancer Society, 1991]. As such, the incidence of oral SCC in tobacco smokers is 4-7 times higher than in non-smokers [see, for example, Ko et al. *J Oral Pathol Med* 1995; 24:450-3].

Various malignancies are particularly associated with smokeless tobacco consumption. These include oral cancer and cancer of the gastrointestinal tract including esophagus and bladder. Leukoplakia, a tobacco induced white patch on the buccal mucosa, as found in smokers, is a localized irritation due to direct contact of smoked or smokeless tobacco and it is directly related to the frequency and years of tobacco abuse. Although leukoplakia is a benign oral lesion, it has a malignant potential.

In addition, tobacco contributes to other oral symptoms or pathologies of the mouth and teeth. Tobacco may cause halitosis, may numb the taste buds, and interfere with the smell and the taste of food. It may stain teeth and contribute to dental caries. Smokers have more dental tartar (calculus) than non-smokers. Tobacco is associated also with destructive periodontal (gum) disease and tooth loss. Acute necrotizing ulcerative gingivitis ("trench mouth") is a destructive, painful inflammatory condition occurring mainly in tobacco smokers. Swelling of the nasal and sinus membranes has also been associated, purportedly, in individuals who are "allergic" to TS.

Oral submucous fibrosis occurs mainly in India and is a chronic, progressive premalignant condition. The etiology is chronic chewing of tobacco or *areca* nut or both. The fibrosis results in restriction of mouth opening and involves the palates, tonsillar fossa, buccal mucosa and underlying muscle. Associated with this condition are also oropharyngeal carcinomas, also with a high frequency in India and associated in 70% of cases with chewing tobacco. Smokeless tobacco and areca nut usage is also common in Pakistan, Bangladesh and Java and in these and Indian immigrants to the United States and United Kingdom.

Studies have estimated that TS has over 3,000 different constituents, of which many are toxic, carcinogenic and/or generate free radical species.

Free radicals are atoms or molecules containing an unpaired electron. Oxygen free radicals include the superoxide free radical ($.O_2^-$) and the hydroxyl radical (OH.) which, together with hydrogen peroxide ($H_2O_2$) and singlet oxygen ($^1O_2$), are jointly called reactive oxygen species (ROS). Due to their high reactivity they may lead to chemical modification and impairment of the components of living cells, such as proteins, lipids, carbohydrates and nucleotides.

Tobacco smoke therefore induces oxidative damage to lipids, DNA and proteins, particularly via protein-SH groups as a consequence of containing high levels of both free radicals as well as aldehydes, including acetaldehyde (ethanol), propanol and acrolein, as well as other deleterious molecules.

Most of constituents of TS have been identified in so-called mainstream and side stream TS. The former is that volume of smoke drawn through the mouthpiece of the tobacco product during puffing while side stream smoke is that smoke emitted from the smoldering cigarette in between puffs. Although tar and nicotine are retained in the filter of cigarettes, this applies mainly to mainstream smoke, when comparing filter and non-filter cigarettes. Mainstream smoke emission is also markedly reduced both in low and in ultra low tar yield cigarettes. However, the emissions of toxic and carcinogenic components in side stream smoke are not significantly reduced in filter cigarettes when compared to non-filter counterparts. Thus, side stream smoke is a major contributor to environmental smoke, affecting both the smoker and their non-smoking counterparts, so called secondary smokers.

Tobacco smoke is divided into two phases; tar and gas-phase smoke. Tar contains high concentrations of free radicals. Many tar extracts and oxidants are water-soluble and reduce oxygen to superoxide radical which can dismutate to form the potent oxidant $H_2O_2$. Oxidants in gas-phase smoke are reactive carbon- and oxygen-centered radicals with extremely short half lives.

Cells subjected to oxidative stress develop severely affected cellular function and suffer damage to membrane lipids, to proteins, to cytoskeletal structures and to DNA. Free radical damage to DNA has been measured as formation of single-strand breaks, double-strand breaks and chromosomal aberrations. Cells exposed to ionizing radiation and TS have also been demonstrated to have an increased intracellular DNA damage, a precursor of mutations and development of malignancies. It has been shown that TS elicits protein carbonylation in plasma and that, in contrast, exposure of human plasma to gas-phase but not to whole TS produces oxidative damage to lipids.

Glutathione, a sulfur-containing tripeptide (L-glutamyl-1-cysteine-glycine) is the most abundant non-protein thiol in mammalian cells and is recognized as the primordial antioxidant. Glutathione, in its reduced form, "GSH", acts as a substrate for glutathione-S-transferase and glutathione peroxidase, enzymes catalyzing reactions involved in detoxification of xenobiotic compounds and in antioxidation of ROS and other free radicals. This ubiquitous protein plays a vital function in maintaining the integrity of free radical sensitive cellular components. Under states of GSH depletion, including malnutrition and severe oxidative stress, cells may then become injured from excess free radical damage and die.

The translocator protein (TSPO) receptor, formerly known as the peripheral-type benzodiazepine receptor (PBR), is an 18-kDa protein located primarily in the outer mitochondrial membrane. TSPO is also referred to in the art as mitochondrial diazepam binding inhibitor (DBI) receptor complex, PK11195-binding sites, isoquinoline-binding protein (IBP), benzodiazepine receptor peripheral, pk18 and ω3 receptor. TSPO receptor is one of a group of proteins that compose the mitochondrial permeability transition pore (MPTP) complex. A background art schematic illustration of MPTP and the pathways associated therewith is presented in FIG. 1.

The MPTP complex of proteins play a central role in various physiological and pathological processes including apoptosis, ischemia, regulation of the mitochondrial membrane potential, mitochondrial respiration, steroidogenesis, immune responses of the cardiovascular system, cell proliferation, and cancer. Other known proteins of the MPTP complex are the 32-kDa voltage dependent anion channel (VDAC) and the 30-kDa adenine nucleotide transporter (ANT). A number of TSPO molecules can be linked to one VDAC molecule. The TSPO receptor can also function without interacting with VDAC and ANT. Additional molecules, such as pk10 (protein of 10 kDa), PBR associated protein1 (PRAX-1) and PBR associated protein 7 (PAP7) can be linked to the TSPO receptor.

TSPO receptor plays an important role in enhancing the ability of cells and tissues to manage ROS-induced damage. Moreover, astrocytes may increase their TSPO expression in hyperammonemia in an attempt to suppress or defend against hyperammonemia associated with increase in ROS production. In addition, TSPO is preferentially expressed in superficial keratinocytes of the differentiated layers of normal epidermis. This preferential expression may be linked to a mechanism of skin protection against ROS damage generated by ultraviolet exposure, as TSPO reduces production of ROS and apoptosis induced by ultraviolet light.

WO 2008/073130 teaches methods for reducing symptoms of conditions whose activity is mediated by TSPO and the cannabinoid $CB_2$ receptors, including inhibition of anxiety, of growth of cancer cells expressing TSPO receptors, and reducing oxygen radical damage to cells, by contacting the cells with the TSPO and the cannabinoid $CB_2$ receptors agonist cis-epoxyeicosatrienoic acid, an inhibitor of soluble epoxide hydrolase (sEH), or both.

Several ligands of TSPO are known. These include benzodiazepine derivatives [e.g. diazepam and 4-chlorodiazepam (Ro5 4864)], isoquinolone carboxamide derivatives (e.g. PK 11195), 2-aryl-3-indoleacetamide derivatives (e.g. FGIN-1), pyrrolobenzoxazepine derivatives, phenoxyphenyl-acetamide derivatives, pyridazinoindole derivatives and 8-oxodihydropurine derivatives. Interestingly, the TSPO does not bind the central benzodiazepine receptor ligand clonazepam. In addition to these high affinity ligands, dicarboxylic porphyrins also bind to the TSPO protein and, although they have lower affinity, it has been proposed that they serve as endogenous ligands (e.g. protoporphyrin IX and hemoglobin). Other endogenous ligands of the TSPO protein are the 86 amino acid polypeptide—endozepine, found in central and peripheral tissue, diazepam-binding inhibitor and its metabolite triakontatetraneuropeptide (TTN), $PLA_2$ and cholesterol. The high affinity binding of cholesterol to TSPO is essential for the process of steroid and bile salt biosynthesis and the low affinity binding of porphyrin is important for the process of heme biosynthesis.

TSPO has been found to be involved in different pathological conditions such as ischemia-reperfusion injury, brain injury, a certain form of epilepsy, neurodegenerative disorders (e.g. Alzheimer's disease, Parkinson's disease), peripheral neuropathy, psychiatric disorders (e.g. anxiety, posttraumatic stress disorder, schizophrenia) and cancer.

Benzodiazepines (BZ's) are a class of lipophilic molecules comprising a benzene ring. To date, there are more then 20 benzodiazepines in clinical use having hypnotic, sedative, anxiolytic, anticonvulsant, muscle relaxant and amnesic properties. These effects are mediated via the central benzodiazepine receptor (CBR). Benzodiazepines are positive allosteric modulators of GABA and bind to a specific subunit of the $GABA_A$ receptor [also called the central benzodiazepine receptor (CBR)] and activate it, leading to decreased neurological activity. In order for $GABA_A$ receptors to be sensitive to the action of benzodiazepines, they need to contain both an α and a γ subunit. Some BZs, such as diazepam, also binds to the TSPO receptor in peripheral tissues.

Diazepam (Valium) is a benzodiazepine derivative drug that possesses anxiolytic, anticonvulsant, sedative, skeletal muscle relaxant and amnestic properties. It is commonly used for treating anxiety, insomnia, seizures, alcohol withdrawal, and muscle spasms.

TSPO receptor ligands have been described as therapeutically active agents for various uses.

For example, U.S. Pat. No. 7,220,739 teaches methods for treating a condition associated with disregulation of the process of cell death in a subject, comprising administrating to the subject an effective amount of a benzodiazepine compound. The benzodiazepines taught in this patent are identified by their inability to bind to CBR and by low affinity to TSPO. The conditions associated with deregulation of the process of cell death taught in this patent include autoimmune diseases such as systemic lupus erythematosus, rheumatoid arthritis, Sjögren's syndrome, graft-versus host disease, and myasthenia gravis; chronic inflammatory conditions such as psoriasis, asthma and Chrones disease; hyperproliferative disorders of neoplasm's such as B-cell or T-cell lymphoma; viral infection and other conditions such as osteoarthritis and atherosclerosis. According to the teachings of U.S. Pat. No. 7,220,739, the therapeutic potential of benzodiazepines is due to their proapoptotic and cytotoxic properties.

Sakai et al. [*European Journal of Pharmacology* 2006; 550:8-14] describe cell proliferation inducing properties of TSPO ligands in tumor cells. Sakai et al. suggest that discrepancies regarding the observed role of TSPO ligands in cell proliferation, seem to rely on the doses of TSPO ligands used, wherein subjecting the cells to low concentrations of TSPO ligands (nM) leads to an increase in cell proliferation whereas high concentration (μM) inhibits cell proliferation.

The present inventors have recently synthesized ligands of the TSPO receptor for the treatment and prevention of brain damage due to traumatic brain injury (TBI) and for the treatment and prevention of neurodegenerative diseases (see, WO 2008/023357). The compounds taught in WO 2008/023357 are quinoxaline, quinazoline and phthalazine derivatives, as well as multimeric compounds. According to the teachings of WO 2008/023357, the compounds described therein bind to TSPO, reduce basal apoptotic levels in neuronal cells, as well as apoptosis induced by glutamate. Glutamate is known as an important agent which causes secondary brain damage after traumatic brain damages, and is also involved in neurodegenerative diseases.

U.S. Pat. No. 5,550,124 teaches agonists of TSPO for the prevention and treatment of various central nervous system (CNS) injuries. This patent also teaches methods of screening for new TSPO agonists.

U.S. Pat. No. 5,776,946 teaches the use of compounds which bind with high affinity to TSPO receptor as anti-inflammatory agents. Such compounds include isoquinoline and benzodiazepine derivatives. Inflammatory conditions treatable by these compounds, as taught by this patent, include rheumatoid arthritis, lupus erythematosus, Sjogren's syndrome, osteoarthritis, multiple sclerosis, Behcet's disease, temporal arthritis and dementia of the Alzheimer type.

U.S. Pat. No. 6,686,354 teaches use of agonists and antagonists of TSPO to induce or inhibit cardiac hypertrophy. In particular, this patent teaches use of antagonists of TSPO in the prevention or treatment of decompensated cardiac hypertrophy and eventually, heart failure. U.S. Pat. No. 6,686,354 also teaches the use of TSPO agonists in the management of conditions calling for increased blood flow or cardiac output such as injury or functional compromise, of the heart, increased demand for physical exercise by athletes or by those who need extra help to improve cardiac performance as a result of a disability, existing atrio-ventricular (A-V) shunts, an acquired or inherited predisposition to cardiac contractile protein dysfunction.

U.S. Pat. No. 7,267,977 describes the involvement of TSPO in human breast cancer, wherein the invasive and metastatic ability of human breast tumor cells is proportional to the level of TSPO expressed and correlates with the subcellular localization of TSPO in these cells. According to the teachings of this patent, TSPO is found primarily in the nuclei of aggressive tumor cells whereas TSPO is found primarily in the cytoplasm of invasive but non-aggressive cells. U.S. Pat. No. 7,267,977 teaches methods for detecting the level of metastatic ability of cells by measuring the level of TSPO in tumor cells as compared to normal cells. U.S. Pat. No. 7,267,977 also teaches methods and compositions effective for reducing or inhibiting TSPO expression or function, for use as a treatment for metastatic breast cancer. The compositions taught by this patent comprise antibodies or compounds capable of reducing or inhibiting TSPO such as TSPO antagonists as well as various ions, anions, phospholipids and factors which affect the stability of the TSPO receptor.

Other suggested therapeutical applications for TSPO receptor ligands include topical use in the treatment of skin (cutaneous) stress (see, U.S. Pat. No. 6,767,533) and treatment of neuropathic pain (see, EP patent application No. 06732484.8, International publication No. WO 2006/115302).

U.S. Pat. No. 6,379,649 teaches imidazo(1,2-a)pyridines and related compounds, for the treatment and detection of disorders that are characterized by an abnormal density of TSPO receptors such as neurodegenerative disorders and tumors.

Several prior art approaches have been employed in order to reduce or prevent incidence of oral disease resulting from oxidant injury.

For example, cigarette filters are used to trap TS tar but do not affect the gas-phase compounds.

One approach has employed a filter for TS providing chemoabsorptive properties to reduce aldehyde concentration in TS (see, U.S. Pat. No. 5,060,672).

Another approach has employed oral megadoses of antioxidants in attempts to reduce generation of $H_2O_2$ resulting from the "respiratory burst" reaction associated with phagocytic activity of macrophages and neutrophils. It has been shown that smokers have a higher "respiratory burst" reaction than non-smokers and that this may be associated with the increased incidence of aerodigestive tract disease in the former.

In yet another approach, dipeptide compounds with pharmaceutical properties to increase glutathione levels were employed (see, for example, U.S. Pat. No. 4,761,399).

A further approach utilized a glycine carboxylic acid alkyl mono-ester of glutathione to increase cellular GSH levels (see, for example, U.S. Pat. No. 4,710,489).

In yet a further approach, administration of a combination of glutathione and selenium was suggested for preventing oxidant injury resulting from exposure to TS (see, for example, U.S. Pat. No. 5,922,346).

In another approach, administration of a combination of glutathione, ascorbic acid, selenium and a sulfur-containing amino acid was suggested in order to prevent oral oxidant injury (see, for example, U.S. Pat. No. 6,228,347).

In yet another approach, administration of a combination including some or all of the following antioxidants; L-glutathione, L-selenomethionine, L-selenocysteine, ascorbyl palmitate, ascorbic acid esters, L-cysteine, N-acetyl-1-cysteine, tocopherol acetate, tocopherol succinate, vitamin A, a zinc salt, methionine and taurine was suggested in order to provide intra-oral protection from oxidant injury (see, U.S. Pat. No. 5,829,449).

The present inventors have previously described novel smoking filters and oral compositions for reducing tobacco associated damage in the aerodigestive tract (see, U.S. Pat. No. 6,789,546, which is incorporated by reference as if fully set forth herein). These compositions include active agents which are capable of reducing or preventing tobacco associated loss of peroxidase activity in the aerodigestive tract.

U.S. Pat. No. 5,922,346 teaches a composition for reducing free radical damage induced by tobacco products and environmental pollutants comprising, as active ingredients, reduced glutathione and a source of selenium selected from the group consisting of elemental selenium, selenomethionine and selenocysteine, the active ingredients being combined with suitable carriers and flavorings for their intra-oral administration as gels, lozenges, tablets and gums in concentrations for reducing free radical damage induced by tobacco products and other environmental pollutants to the oral cavity, pharynx and upper respiratory tract of a user and secondary smokers.

U.S. Pat. No. 5,906,811 teaches a method for reducing free radical damage induced by tobacco products and environmental pollutants comprising administering in a suitable carrier in concentrations for effectively reducing said free radical damage to the oro-pharynx and upper respiratory tract of a user a combination of from 0.01 and 10% (weight) glutathione, from 1.0 to 25% (weight) ascorbic acid, from 0.001 to 10% (weight) of a source of selenium and from 0.001 to 2.0% (weight) of a sulfur containing amino acid.

These aforementioned attempts to reduce tobacco damage are used as an adjuvant treatment following or prior to tobacco consumption, but not concomitantly with tobacco consumption.

U.S. Pat. No. 6,138,683 teaches a composition for inclusion within a quantity of smokeless tobacco, selected from the group consisting of chewing tobacco and snuff, for reducing free radical induced damage to the oro-pharyngeal cavity of the user, said composition comprising L-glutathione and a source of selenium in combination with said smokeless tobacco.

PCT/IL2008/000101, by the present assignee, describes methods, pharmaceutical compositions, oral compositions, filters and tobacco products for preventing or reducing tobacco smoke-associated injury in the aerodigestive tract of a subject, which can be used to prevent or reduce loss of OPO activity or $CN^-$, redox-active metal ion- or aldehyde-induced cell death resulting from TS-associated oxidative stress. Some of the agents described in this document are $CN^-$ chelators and iron chelators.

PCT/IL2008/000628, by the present inventors, describes compositions, articles and methods comprising copper chelating agents such as, for example, penicillamine, as well as structural analogs thereof, for the treatment of tobacco-associated damage.

SUMMARY OF THE INVENTION

The prior art fails to teach or suggest a role for TSPO receptor ligands in the treatment of physiological disorders associated with oxidative stress, let alone diseases and disorders associated with tobacco-induced damage.

The present inventors have surprisingly uncovered that TSPO receptor ligands such as, for example, diazepam, beneficially affect tobacco-associated cellular and macromolecular damage induced by exposure to tobacco smoke, and thus can serve as potent agents for treating and for protecting against oxidative stress-associated and tobacco-associated damage. Thus, according to embodiments of the present invention, TSPO ligands can be, for example, incorporated in tobacco products, food additives and the like, so as to provide a protective effect against active or passive exposure to tobacco smoke and/or to provide a therapeutic effect for treating damages caused by active or passive exposure to tobacco smoke. TSPO ligands can further be utilized as medicaments for treating, or protecting against, disorders associated with active or passive exposure to tobacco smoke, such as COPD, lung and oral cancer, asthma and many more. According to an aspect of some embodiments of the present invention there is provided an article of manufacturing comprising tobacco and a tobacco packaging material, wherein at least a portion of the tobacco and/or tobacco packaging material comprises a TSPO receptor ligand.

According to an aspect of some embodiments of the present invention there is provided an article of manufacturing comprising tobacco and an agent being incorporated in at least a portion of the tobacco, the agent being a TSPO receptor ligand.

According to an aspect of some embodiments of the present invention there is provided an article of manufacturing comprising a tobacco packaging material and an agent being incorporated in at least a portion of the tobacco packaging material, the agent being a TSPO receptor ligand.

According to some embodiments of the invention, the TSPO receptor ligand is such which enables a concentration of the ligand, at the site of the TSPO receptors in a mammalian tissue, to be in the subnanomolar range.

According to some embodiments of the invention the TSPO receptor ligand binds to a homotetrameric form of the TSPO receptor.

According to some embodiments of the invention the TSPO receptor ligand is selected from the group consisting of a benzodiazepine, an isoquinoline carboxamide, an imidazopyridine, a 2-aryl-3-indolacetamide (FGIN-1) a pyrolobenzoxazepines, 2-phenyl-imidazo(1,2-a)pyridine derivatives, phenoxyphenyl-acetamide derivatives, and 8-oxodihydropurine derivatives.

According to some embodiments of the invention the TSPO receptor ligand is a benzodiazepine.

According to some embodiments of the invention the TSPO receptor ligand is diazepam.

According to some embodiments of the invention the TSPO receptor ligand has the general Formula I:

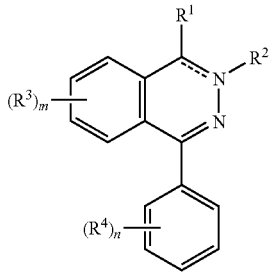

Formula I or a pharmaceutically acceptable salt thereof,
wherein:
$R^1$ is oxo, $R^2$ is a group of the formula A and ----- is a single bond; or
$R^1$ is a group of the formula A, $R^2$ is absent and ----- is a double bond

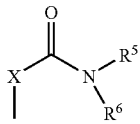

A $R^3$ and $R^4$ are each independently selected from the group consisting of a linear or branched $C_1$-$C_6$ alkyl, a linear or branched $C_2$-$C_6$ alkenyl, a $C_3$-$C_8$ cycloalkyl, heterocyclyl, aryl, heteroaryl, halide, hydroxy, alkoxy, aryloxy, amine, cyano and nitro;
$R^5$ and $R^6$ are each independently selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl;
X is selected from the group consisting of a bond, —O—, —S—, $NR^7$ and —$CR^8R^9$, wherein $R^7$, $R^8$ and $R^9$ are each independently selected from the group consisting of hydrogen and a linear or branched $C_1$-$C_6$ alkyl;
m is an integer from 0 to 4; and
n is an integer from 0 to 5.
According to some embodiments of the invention the TSPO receptor ligand has the general Formula II:

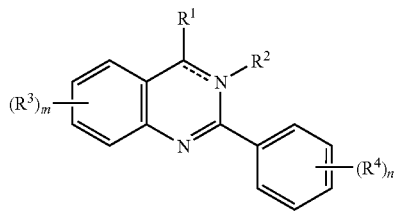

Formula II or a pharmaceutically acceptable salt thereof,
wherein:
$R^1$ is oxo, $R^2$ is a group of the formula A and ----- is a single bond; or
$R^1$ is a group of the formula A, $R^2$ is absent and ----- is a double bond

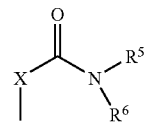

A $R^3$ and $R^4$ are each independently selected from the group consisting of a linear or branched $C_1$-$C_6$ alkyl, a linear or branched $C_2$-$C_6$ alkenyl, a $C_3$-$C_8$ cycloalkyl, heterocyclyl, aryl, heteroaryl, halide, hydroxy, alkoxy, aryloxy, amine, cyano and nitro;
$R^5$ and $R^6$ are each independently selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl;
X is selected from the group consisting of a bond, —O—, —S—, $NR^7$ and —$CR^8R^9$, wherein $R^7$, $R^8$ and $R^9$ are each independently selected from the group consisting of hydrogen and a linear or branched $C_1$-$C_6$ alkyl;
m is an integer from 0 to 4; and
n is an integer from 0 to 5.
According to some embodiments of the invention the TSPO receptor ligand has the general Formula III:

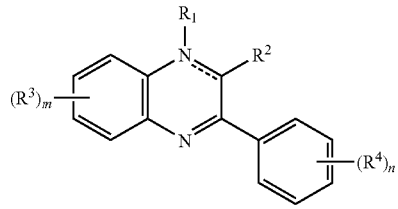

Formula III or a pharmaceutically acceptable salt thereof,
wherein:
$R^1$ is absent, $R^2$ is a group of the formula A and ----- is a double bond; or
$R^1$ is a group of the formula A, $R^2$ is oxo and ----- is a single bond

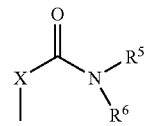

A $R^3$ and $R^4$ are each independently selected from the group consisting of a linear or branched $C_1$-$C_6$ alkyl, a linear or branched $C_2$-$C_6$ alkenyl, a $C_3$-$C_8$ cycloalkyl, heterocyclyl, aryl, heteroaryl, halide, hydroxy, alkoxy, aryloxy, amine, cyano and nitro;
$R^5$ and $R^6$ are each independently selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl;
X is selected from the group consisting of a bond, —O—, —S—, $NR^7$ and —$CR^8R^9$, wherein $R^7$, $R^8$ and $R^9$ are each independently selected from the group consisting of hydrogen and a linear or branched $C_1$-$C_6$ alkyl;
m is an integer from 0 to 4; and
n is an integer from 0 to 5.

According to some embodiments of the invention the TSPO receptor ligand has the general Formula IV:

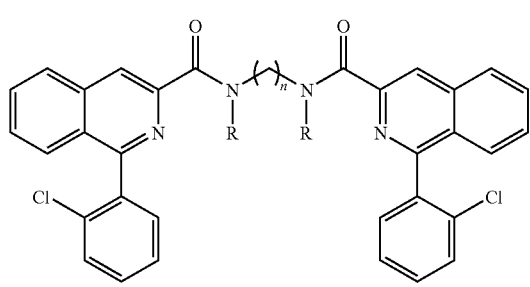

Formula IV or a pharmaceutically acceptable salts thereof,
wherein:
n is an integer of from 1 to 12; and
R is independently selected from the group consisting of a hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl.

According to some embodiments of the invention the TSPO receptor ligand is selected from the group consisting of 1-(2-chlorophenyl)-N-methyl-N-(1-methylpropyl)-3-isoquinoline carboxamide (PK11195), (−)-N,N-dimethyl-2-methyl-3-[4-(2-phenyl)quinolinyl]propaneamide (PK14067) (+)-N,N-dimethyl-2-methyl-3-[4-(2-phenyl)quinolinyl]propaneamide (PK 14068); 1-(2-fluoro-5-nitrophenyl)-N-methyl-N-(1-methylpropyl)-3-isoquinolinecarboxyamide (PK 14105); Ro5-6993, Ro5-4864 (4-chlorodiazepam), Ro5-6900, Ro5-6945, Ro5-6669, Ro5-6902, Ro5-6531, Ro5-3448, Diazepam, Ro7-5520, Ro5-5115, Ro5-4608, Ro5-6524, Ro5-5122, Ro5-3464; 7-chloro-N,N-5-trimethyl-4-oxo-3-phenyl-3,5-dihydro-4H-pyridazino-[4,5-b)] indole-1-acetoamide; FGIN-1-27, alpidem, zolpidem SSR180575, DPA-714, DPA-713, ECO-4601, DAA1097, DAA1106, CB34, CB50, CB54 and pharmaceutically acceptable salts thereof.

According to some embodiments of the invention the TSPO receptor ligand is selected from the group consisting of a dicarboxylic porphyrin, a diazepam-binding inhibitor (DBI), a triakontatetraneuropeptide (TTN), $PLA_2$, endozepine and cholesterol.

According to some embodiments of the invention at least a portion of the tobacco and/or the tobacco packaging material is in contact with an aerodigestive tract of a subject using the article of manufacturing.

According to some embodiments of the invention the TSPO receptor ligand has the general formula V:

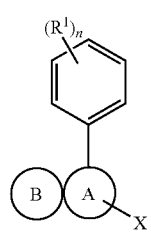

Formula V or a pharmaceutically acceptable salt thereof, wherein:
A is selected from the group consisting of a substituted or unsubstituted five- or six-membered nitrogen-containing heteroalicyclic ring and a substituted or unsubstituted five- or six-membered nitrogen-containing heteroaryl ring; whereas A is linked to the benzene ring via a single covalent bond and the ring contains 1, 2 or 3 nitrogen atoms;

B is a monocyclic or bicyclic ring selected from the group consisting of a substituted or unsubstituted (C5-C6) cycloalkyl ring, a substituted or unsubstituted (C5-C6) heteroalicyclic ring, a substituted or unsubstituted (C5-C6) aryl ring, a substituted or unsubstituted (C5-C6) heteroaryl ring or a combination thereof;

X is —$R^2$—C(═O)—$NR^3R^4$ wherein $R^2$ is absent or is a substituted or unsubstituted C1-C3 alkyl;

$R^3$ and $R^4$ are each independently selected from the group consisting of hydrogen, a substituted or unsubstituted alkyl, a substituted or unsubstituted alkenyl, a substituted or unsubstituted alkynyl, a substituted or unsubstituted cycloalkyl and a substituted or unsubstituted aryl;

$R^1$ is selected from the group consisting of a C1-C3 alkyl, halide, hydroxy, alkoxy, carbonyl, oxo, thiocarbonyl, sulfinyl, sulfonyl, cyano, nitro and —$NR^5R^6$ wherein $R^5$ and $R^6$ are each independently selected from the group consisting of hydrogen and linear or branched alkyl, n is an integer from 1 to 5; and wherein when the A ring or the B is a substituted ring, the substituent is selected from the group consisting of an electronegative group, oxo, thioxo, halide, trihalomethyl, hydroxy, alkoxy, thiohydroxy, thioalkoxy, cyano, nitro, carbonyl, thiocarbonyl, C-carboxylate, O-carboxylate, O-carbamate, N-carbamate, O-thiocarbamate, N-thiocarbamate, sulfinyl, sulfonyl, C-amido, N-amido, amino and —$NR^5R^6$ as defined above.

According to some embodiments of the invention at least one of the A ring and the B ring is a substituted ring, substituted by the electronegative group.

According to some embodiments of the invention the A ring is substituted by oxo or thioxo.

According to some embodiments of the invention the TSPO receptor ligand is capable of suppressing an innate immune activity in a subject using the article of manufacturing.

According to some embodiments of the invention the TSPO receptor ligand is capable of inhibiting inflammation in a subject using the article of manufacturing.

According to some embodiments of the invention the TSPO receptor ligand is capable of reducing or preventing tobacco smoke-associated damage in a subject using the article of manufacturing.

According to some embodiments of the invention at least a portion of the tobacco and/or the tobacco packaging material further comprises at least one additional agent capable of reducing or preventing tobacco smoke-associated damage in a subject using the article of manufacturing.

According to some embodiments of the invention the additional agent is selected from the group consisting of an antioxidant, an iron chelating agent, a cyanide chelating agent and an agent capable of reducing or preventing tobacco associated loss of peroxidase activity in an aerodigestive tract of the subject.

According to some embodiments of the invention the agent is glutathione.

According to some embodiments of the invention the tobacco packaging material comprises a filter and the TSPO receptor ligand is impregnated in a paper of the filter.

According to some embodiments of the invention the tobacco is smokeless tobacco.

According to some embodiments of the invention the tobacco is smoked tobacco.

According to some embodiments of the invention the tobacco packaging material is selected from the group consisting of a rolling paper, a filter paper, a snus bag packaging, a cigarette, a pipe and a tin sheet packaging.

According to some embodiments of the invention the article of manufacturing is selected from the group consisting of a snuff, a cigarette, a snus, a Gutka, a plug, a twist, a scrap and tobacco water.

According to an aspect of some embodiments of the present invention there is provided a method of treating or preventing a physiological disorder associated with oxidative stress, in a subject in need thereof, the method comprising administering to the subject a therapeutically effective amount of a TSPO receptor ligand.

According to an aspect of some embodiments of the present invention there is provided a method of treating or preventing a tobacco-associated damage, in a subject in need thereof, the method comprising administering to the subject a therapeutically effective amount of a TSPO receptor ligand.

According to some embodiments of the invention the therapeutically effective amount is in the subnanomolar range.

According to an aspect of some embodiments of the present invention there is provided use of a TSPO receptor ligand in the manufacture of a medicament for treating or preventing a physiological disorder caused by oxidative stress According to an aspect of some embodiments of the present invention there is provided use of a TSPO receptor ligand in the manufacture of a medicament for treating or preventing a tobacco-associated damage According to some embodiments of the invention the amount of the ligand in the medicament is in the subnanomolar range.

According to an aspect of some embodiments of the present invention there is provided a pharmaceutical composition comprising a TSPO receptor ligand and a pharmaceutically acceptable carrier, the composition being packaged in a packaging material and identified in print, in or on the packaging material, for use in the treatment of a physiological disorder associated with oxidative stress.

According to an aspect of some embodiments of the present invention there is provided a pharmaceutical composition comprising a TSPO receptor ligand and a pharmaceutically acceptable carrier, the composition being packaged in a packaging material and identified in print, in or on the packaging material, for use in the treatment of a tobacco-associated damage.

According to some embodiments of the invention the amount of the ligand in the composition is in the subnanomolar range.

According to some embodiments of the invention the disorder is selected from the group consisting of a neurodegenerative disorder, amyotrophic lateral sclerosis, Huntington's disease, Parkinson's disease Alzheimer's disease, Creutzfeldt-Jakob disease, multiple sclerosis, spongiform encephalopathies, degenerative diseases of the basal ganglia, motoneuron diseases and memory loss; Diabetes, insulin resistance syndrome, retinopathy, blindness, Cataract formation, an infectious disease, a neurological dysfunction following cardiac surgery, a cardiovascular disease, stroke, atherosclerosis, hypertension, coronary heart disease and restenosis; cerebral ischemia, cancer, prostate cancer, bladder cancer, arthritis, chronic obstructive pulmonary disease, paralysis, AIDS, alcohol addiction, periodontitis, inflammatory bowel disease, colorectal disease, chronic kidney disease, alcoholic liver disease, a mitochondrial disease, a metabolic disease, a skin disease, a skin damage, a radiation damage, a damage caused by tobacco use, an excessive angiogenesis, an insufficient angiogenesis, a hearing loss, a collateral damage of chemotherapy and mucositis.

According to some embodiments the amount of the ligand in the composition is in the subnanomolar range.

According to some embodiments of the invention the tobacco-associated damage is effected in a mucosal tissue.

According to some embodiments of the invention the tobacco-associated damage is effected in a non-mucosal tissue.

According to some embodiments of the invention the TSPO receptor ligand is used in combination with at least one additional agent that is capable of reducing or preventing a physiological disorder caused by oxidative stress.

According to some embodiments of the invention the additional agent is an antioxidant.

According to some embodiments of the invention the antioxidant is glutathione.

According to an aspect of some embodiments of the present invention there is provided an article of manufacturing comprising a filter and an agent comprised within the filter, the agent being a TSPO receptor ligand and the filter being designed and configured so as to enable release of the agent therefrom when in use by a subject.

According to an aspect of some embodiments of the present invention there is provided an oral composition comprising a TSPO receptor ligand, the composition being in the form of a toothpaste, powder, liquid dentifrice, mouthwash, denture cleanser, chewing gum, lozenge, paste, gel or candy.

According to some embodiments of the invention the oral composition further comprises a flavorant.

According to an aspect of some embodiments of the present invention there is provided a medical device comprising a TSPO receptor ligand, the medical device being designed and configured to deliver the TSPO receptor ligand to a bodily site.

According to some embodiments of the invention the medical device is for delivering the TSPO receptor ligand by topical or transdermal application.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

As shown in FIG. 5, B values for TSPO receptor binding were significantly reduced, by 30%, in saliva exposed to CS as compared to control. (n=34, p<0.01). The results are expressed as mean values±SE.

FIGS. 9(A-D) present western blot analyses showing the presence of TSPO in SCC-25 (FIG. 9A) and SCC-15 (FIG. 9B) cell lines and bar graphs showing the level of protein carbonylation in SCC-25 (FIG. 9C) and SCC-15 (FIG. 9D) cell lines plotted against cell CS exposure time. The protein carbonylation level is enhanced 6 folds in cells exposed to CS for 30 minutes, as compared to control, non-exposed cells.

DETAILED DESCRIPTION OF EMBODIMENTS OF THE INVENTION

Figure 1:
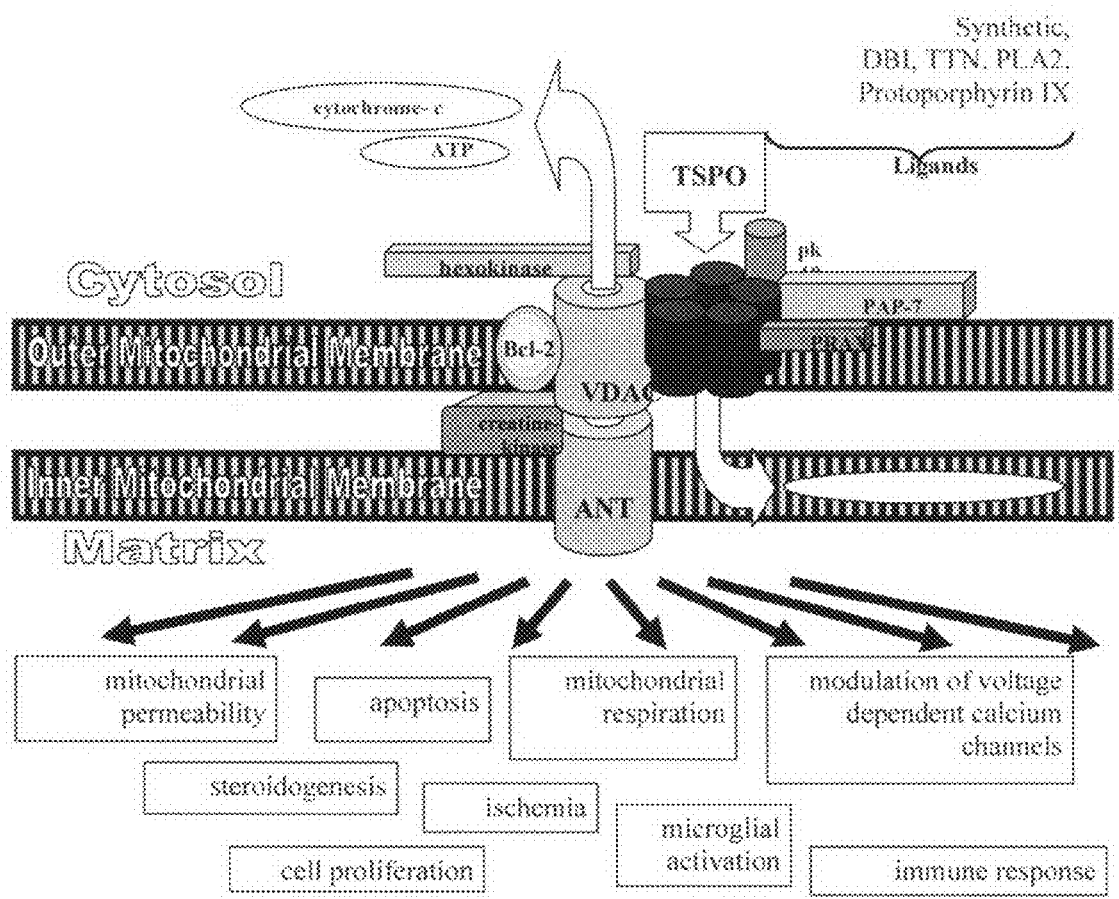
FIG. 1 is a background art schematic illustration showing the location of TSPO and its protein components in the mitochondrial permeability transition pore (MPTP) complex.

The present invention is of articles, methods and compositions for preventing or reducing tobacco smoke-associated damage and/or disorders associated with oxidative stress. Specifically, the present invention, in some embodiments thereof, is of methods, pharmaceutical compositions, oral compositions, medical devices, filters and tobacco products, which are useful in preventing or reducing tobacco smoke-associated damage, as well as preventing or reducing physiological disorders associated with oxidative stress, and which utilize TSPO receptor ligands.

The principles and operation of some embodiments of the present invention may be better understood with reference to the drawings and accompanying examples.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Tobacco consumption, such as in the form of smoking, chewing, dipping or snuffing, is associated with pathogenesis of many diseases.

The present inventors have previously described novel smoking filters and oral compositions for reducing tobacco associated damage in the aerodigestive tract (see, U.S. Pat. No. 6,789,546). These compositions include active agents which are capable of reducing or preventing tobacco associated loss of peroxidase activity in the aerodigestive tract. Some of the present inventors have previously taught tobacco compositions and tobacco packaging means that prevent or reduce loss of OPO activity or CN⁻, redox-active metal ion- or aldehyde-induced cell death resulting from TS-associated oxidative stress (see, PCT/IL2008/000101). The present inventors have previously described compositions, articles and methods comprising copper chelating agents such as, for example, penicillamine, as well as structural analogs thereof, for use in the treatment of tobacco-associated damage (see, PCT/IL2008/000628).

As discussed hereinabove, tobacco consumption may lead to various, severe tobacco-associated damage, which affects millions subjects every year. There is thus a widely recognized need for, and it would be highly advantageous to have, compositions and means for preventing or reducing tobacco-associated damage.

The present inventors have now surprisingly uncovered that translocator protein (TSPO) receptor ligands, such as, for example, diazepam, are highly effective in ameliorating physiological disorders caused by oxidative stress and tobacco-associated damage in particular.

Thus, TSPO receptor ligands (e.g., diazepam), according to the present embodiments, can be efficiently utilized in the manufacture of various articles (e.g., tobacco products, filters, tobacco packaging materials and the like), of pharmaceutical compositions, of oral compositions, of medical devices and of medicaments for reducing or preventing physiological disorders caused by oxidative stress.

The TSPO receptor ligands (e.g., diazepam), according to the present embodiments, can be efficiently utilized in the manufacture of various articles (e.g., tobacco products, filters, tobacco packaging materials and the like), of pharmaceutical compositions, of oral compositions, of medical devices and of medicaments for reducing or preventing physiological disorders caused by tobacco-associated damage.

The term "ligand", as used herein, describes a relatively small molecule that binds, typically reversibly, to a specific binding site found on a macromolecule's surface by intermolecular forces. Ligand binding typically leads to structural changes in the macromolecule, and affects the activity thereof, and hence ligands are also known as allosteric regulators. The structural-conformational change induced by ligand binding typically alters the behavior of the macromolecule. Thus, for example, ligand binding typically results in an altered behavior of a macromolecule-associated ion channel or enzyme, or of other biological pathways in which the macromolecule is involved or affects.

The term "receptor", as used herein, describes a membranal protein, a cytoplasm protein or nucleus protein which is capable of binding a specific molecule (a ligand), such as a neurotransmitter, hormone, or other substance, and initiates a cellular chemical (including an electrochemical) response to the binding event. Ligand-induced changes in the behavior of receptor proteins result in physiological changes that constitute the biological actions of the ligands.

The term "TSPO receptor", as used herein, describes the 18-kDa translocator protein (TSPO), formerly known as the peripheral-type benzodiazepine receptor (PBR), located primarily in the outer mitochondrial membrane. TSPO is also referred to in the art as mitochondrial diazepam binding inhibitor (DBI) receptor complex, PK11195-binding sites, isoquinoline-binding protein (IBP), benzodiazepine receptor peripheral, pk18 and ω3 receptor. TSPO receptor is one of a group of proteins that compose the mitochondrial permeability transition pore (MPTP) complex. A background art schematic illustration of MPTP and the pathways associated therewith is presented in FIG. 1.

As used herein, the phrase "TSPO receptor ligand", is used in the broadest sense to include endogenous or exogenous factors that can interact with a TSPO receptor, including native and synthetic ligands. The term "TSPO receptor ligand" includes antagonist and agonists of the TSPO receptor, as defined hereinbelow.

The term "native ligand" refers to endogenous ligands of TSPO receptor, as defined herein. Such native ligands can be isolated from natural sources or can be produced by recombinant and/or synthetic means.

The phrases "TSPO receptor ligand" and "TSPO ligand" are used herein interchangeably.

The interaction of ligands with their binding sites can be characterized in terms of a binding affinity, wherein high affinity ligand binding results from greater intermolecular forces between the ligand and its binding site, which affect a longer residence time of the ligand at its receptor binding site and a greater physiological effect induced by this interaction, while low affinity ligand binding involves weaker intermolecular forces between the ligand and its binding site, which result in a shorter effecting time.

In some embodiments, the TSPO receptor ligand described herein binds with high affinity to a TSPO receptor in a mammalian tissue.

As used herein, the "high affinity" binding describes a TSPO receptor ligand having a binding affinity, characterized by the value Kd, to the TSPO receptor of at least $10^{-4}$ M, as determined by affinity-binding assays. Such affinity-binding assays are known in the art and are typically conducted in tissue expressing TSPO receptors as described, for example, in Braestrup et al. [*Proc. Natl. Acad. Sci. USA*, 1977; 74: 3805-3809] for brain tissue and in Wang et al. [*Mol. Pharmacol.* 1984; 25: 349-351] for non-brain tissue. The binding affinity assays may be performed by direct binding (Schomaker et al. *J. Pharmacol. Exp. Ther,* 1983; 285:61-69] or by indirect binding such as competitive binding of the tested compound to tissue expressing TSPO receptors in the presence of [$^3$H]PK11195. [$^3$H]PK11195 has a high degree of affinity to TSPO receptors.

In some embodiments, the binding affinity of the TSPO receptor ligand is in the subnanomolar range.

The phrase "subnanomolar range" means a TSPO receptor ligand with a Kd value that ranges from $10^{-8}$ M to $10^{-9}$ M.

The term "mammalian tissue" describes a cell, including components thereof, a tissue (including fluid tissues such as blood) or an organ of a mammal such as a human being.

As used herein, the term "agonist" describes a substance that is capable of binding to a receptor and thereby initiating a physiological activity or pathway associated with the receptor.

As used herein, the term "antagonist" describes a substance that acts within the body to reduce the physiological activity of another substance, such as an agonist. An antagonist can thus act as a competitive receptor ligand or can otherwise inhibit the binding of an agonist to a receptor.

As discussed hereinabove, a TSPO receptor ligand according to embodiments of the present invention can be a native ligand (e.g., endogenous ligand) or a synthetic ligand.

According to some embodiments, the TSPO receptor ligand may bind both to a monomeric as well as to a polymeric complex of the TSPO receptor. In some embodiments, the TSPO receptor ligand binds to a homotetrameric TSPO receptor complex having a MW of 72 kDa.

According to some embodiments, the TSPO receptor ligand may bind to TSPO wherein the TSPO is in complex with additional proteins (for example, VDAC).

There are several native TSPO ligands. Some of the currently identified TSPO native ligands include, but are not limited to, diazepam-binding inhibitor (DBI), naturally occurring dicarboxylic porphyrins, the 86 amino acid polypeptide endozepine, found in central and peripheral tissue, diazepam-binding inhibitor and its metabolite triakontatetraneuropeptide (TTN), PLA$_2$ and cholesterol.

Synthetic ligands of the TSPO receptor are also known and characterized. Exemplary TSPO ligands include, but are not limited to, 1-(2-chlorophenyl)-N-methyl-N-(1-methylpropyl)-3-isoquinoline carboxamide (PK11195), (−)-N,N-dimethyl-2-methyl-3-[4-(2-phenyl)equinolinyl]propaneamide (PK14067) (+)-N,N-dimethyl-2-methyl-3-[4-(2-phenyl)quinolinyl]propaneamide (PK 14068); 1-(2-fluoro-5-nitrophenyl)-N-methyl-N-(1-methylpropyl)-3-isoquinolinecarboxamide (PK 14105); Ro5-6993, Ro5-4864 (4-chlorodiazepam), Ro5-6900, Ro5-6945, Ro5-6669, Ro5-6902, Ro5-6531, Ro5-3448, Diazepam, Ro7-5520, Ro5-5115, Ro5-4608, Ro5-6524, Ro5-5122, Ro5-3464; 7-chloro-N,N-5-trimethyl-4-oxo-3-phenyl-3,5-dihydro-4H-pyridazino-[4,5-b]indole-1-acetoamide; FGIN-1-27, alpidem, zolpidem SSR180575, DPA-714, DPA-713, ECO-4601, DAA1097, DAA1106, CB34, CB50 and CB54.

Ro5-4685, Ro5-4864, PK11195, PK14105 are described in Cox et al. [J. Pharmacol. Exp. Ther. 1991; 258:702-709;]; DAA1106, DPA-714, DPA-713 are described in James et al. [Journal of Nuclear Medicine 49:5814-5822]; PK11195, PK14105, Ro5-4864, Ro5-6900, Ro5-6945, Ro5-6669, Ro5-6902, Ro5-6531, Ro5-3448, Diazepam, Ro7-5520, Ro5-5115, Ro5-4608, Ro5-6524, Ro5-5122, Ro5-3464 are described in U.S. Pat. No. 5,550,124; ECO-4601 is described in Gourdeau et al. [Cancer Chemotherp Pharmacol 2008;

61:911-921]; 7-chloro-N,N-5-trimethyl-4-oxo-3-phenyl-3,5-dihydro-4H-pyridazino-[4,5-b]indole-1-acetoamide and SSR180575 are described in European Patent No. 1878443. The chemical structures of PK11195, PK14105, PK14067/8, alpidem, zolpidem, Ro5-4864, FGIN-1-27, DPA-714, SSR180575, CB34, CB50, CB54, DAA1097, DAA1106, clonazepam, flunitrazepam and diazepam are presented in FIG. 3.

According to some embodiments, exemplary TSPO receptor ligands suitable for use in the various aspects of the present invention include, but are not limited to, benzodiazepines (for example diazepam), isoquinoline carboxamides (for example PK11195), imidazopyridines, 2-aryl-3-indolacetamides (for example FGIN-1) pyrolobenzoxazepines, 2-phenyl-imidazo (1,2-a)pyridine derivatives, phenoxyphenyl-acetamide derivatives, and 8-oxodihydropurine derivatives.

By "derivatives" it is meant that the compound has the indicated skeleton, namely, is a 2-phenyl-imidazo(1,2-a)pyridine, a phenoxyphenyl-acetamide or a 8-oxodihydropurine, which is optionally substituted by one or more substituents.

Benzodiazepines are well known TSPO ligands (previously named peripheral benzodiazepine receptor). The term "benzodiazepine" describes a seven-membered non-aromatic heterocyclic ring (also referred to herein as heteroalicyclic) fused to a phenyl ring wherein the seven-membered ring has two nitrogen atoms, as part of the heterocyclic ring. In some embodiments, the two nitrogen atoms are in 1 and 4 positions, as shown in the general structure below.

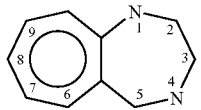

The benzodiazepine can be substituted with one keto group (typically in the 2-position), or with two keto groups (one each at the 2 and 5 position). Most generally, the benzodiazepine is further substituted either on the phenyl ring or on the seven membered heterocyclic ring or on both rings by a variety of substituents.

The term "keto" describes a —C(=O)— group, and is also referred to herein as an "oxo" substituent.

The benzodiazepine Ro5-4864 (4'-chlorodiazepam) binds with high affinity to the TSPO receptor from rodent species and with low affinity to the central type-GABA receptors (CBR). Conversely, Clonazepam and Flumazenil, which bind with high affinity to the "central" type, exhibit low affinity for the "peripheral" type TSPO. PK-11195 has high affinity (Kd<20 nM) for the TSPO receptor. PK11195 was classified as an antagonist for TSPO receptor, whereas Ro5-4864 as agonist. However, those ligands can induce similar effects under some physiological condition. The Imidazopyridines, another series of ligands, bind both the TSPO receptor in peripheral tissues and the CBR. The TSPO-specific ligands, FGIN-1-27, display high affinity to TSPO and low affinity to CBR. Isoquinolines, like PK 11195, bind specifically and exclusively to the TSPO receptor whereas benzodiazepine ligands, Ro5-4864, for example, interact with TSPO receptors, associated with one molecule of VDAC.

The TSPO receptor ligand, according to embodiments of the present invention, does not encompass a benzodiazepine (such as clonazepam), or any other ligand, which binds with high affinity to central benzodiazepine receptor but do not bind or bind with low affinity to the TSPO receptor (a peripheral benzodiazepine receptor).

As demonstrated in the Examples section that follows, an exemplary benzodiazepine TSPO receptor ligand, diazepam, was found to be highly effective in decreasing the level of cell death due to oxidative stress induced by exposure to cigarette smoke. As opposed to diazepam, clonazepam was found to enhance the level of cell death, indicating a role of a TSPO receptor in the mechanism responsible for the diazepam-protective activity. Diazepam was shown to reduce cell death due to oxidative stress induced by exposure to tobacco smoke, in the presence of saliva, thus suggesting that its activity is related to salivary enzymes.

According to some embodiments, the TSPO receptor ligands include, but are not limited to, quinoxaline, quinazoline and phthalazine derivatives such as those described in WO 2008/023357, which is incorporated by reference as if fully set forth herein.

Thus, according to some embodiments, the TSPO receptor ligands include, but are not limited to, compounds having the general Formula I:

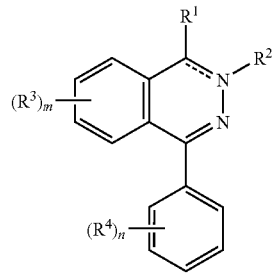

Formula I including pharmaceutically acceptable salts thereof, wherein:

$R^1$ is oxo, $R^2$ is a group of the formula A and ----- is a single bond; or $R^1$ is a group of the formula A, $R^2$ is absent and ----- is a double bond

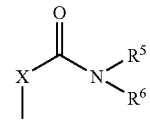

A $R^3$ and $R^4$ are each independently selected from the group consisting of a linear or branched $C_1$-$C_6$ alkyl, a linear or branched $C_2$-$C_6$ alkenyl, a $C_3$-$C_8$ cycloalkyl, heterocyclyl, aryl, heteroaryl, halide, hydroxy, alkoxy, aryloxy, amine, cyano and nitro;

$R^5$ and $R^6$ are each independently selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl;

X is selected from the group consisting of a bond, —O—, —S—, $NR^7$ and —$CR^8R^9$, wherein $R^7$, $R^8$ and $R^9$ are each independently selected from the group consisting of hydrogen and a linear or branched $C_1$-$C_6$ alkyl;

m is an integer from 0 to 4; and n is an integer from 0 to 5.

According to some embodiments, the TSPO receptor ligands include, but are not limited to, compounds having the general Formula II:

Formula II

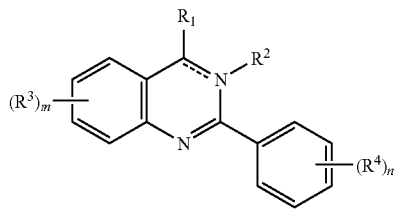

including pharmaceutically acceptable salts thereof, wherein:

$R^1$ is oxo, $R^2$ is a group of the formula A and ----- is a single bond; or $R^1$ is a group of the formula A, $R^2$ is absent and ----- is a double bond

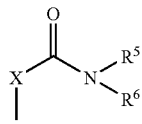
A $R^3$ and $R^4$ are each independently selected from the group consisting of a linear or branched $C_1$-$C_6$ alkyl, a linear or branched $C_2$-$C_6$ alkenyl, a $C_3$-$C_8$ cycloalkyl, heterocyclyl, aryl, heteroaryl, halide, hydroxy, alkoxy, aryloxy, amine, cyano and nitro;

$R^5$ and $R^6$ are each independently selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl;

X is selected from the group consisting of a bond, —O—, —S—, $NR^7$ and —$CR^8R^9$, wherein $R^7$, $R^8$ and $R^9$ are each independently selected from the group consisting of hydrogen and a linear or branched $C_1$-$C_6$ alkyl;

m is an integer from 0 to 4; and n is an integer from 0 to 5.

According to some embodiments, the TSPO receptor ligands include, but are not limited to, compounds having the general Formula III:

Formula III

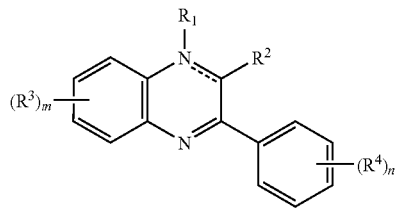

including pharmaceutically acceptable salts thereof, wherein:

$R^1$ is absent, $R^2$ is a group of the formula A and ----- is a double bond; or $R^1$ is a group of the formula A, $R^2$ is oxo and ----- is a single bond

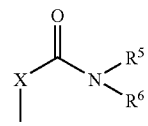
A $R^3$ and $R^4$ are each independently selected from the group consisting of a linear or branched $C_1$-$C_6$ alkyl, a linear or branched $C_2$-$C_6$ alkenyl, a $C_3$-$C_8$ cycloalkyl, heterocyclyl, aryl, heteroaryl, halide, hydroxy, alkoxy, aryloxy, amine, cyano and nitro;

$R^5$ and $R^6$ are each independently selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl;

X is selected from the group consisting of a bond, —O—, —S—, $NR^7$ and —$CR^8R^9$, wherein $R^7$, $R^8$ and $R^9$ are each independently selected from the group consisting of hydrogen and a linear or branched $C_1$-$C_6$ alkyl;

m is an integer from 0 to 4; and n is an integer from 0 to 5.

According to some embodiments, the TSPO receptor ligands include, but are not limited to, compounds having the general Formula IV:

Formula IV

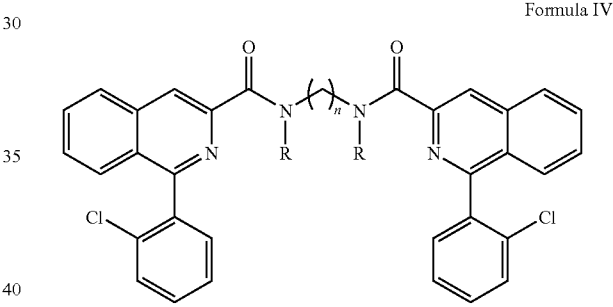

including pharmaceutically acceptable salts thereof, wherein:

n is an integer of from 1 to 12; and

R is independently selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl.

Other features of TSPO receptor ligands having the general Formulae I, II, III and IV hereinabove, according to embodiments of the present invention, are described in WO 2008/023357.

Figure 3:
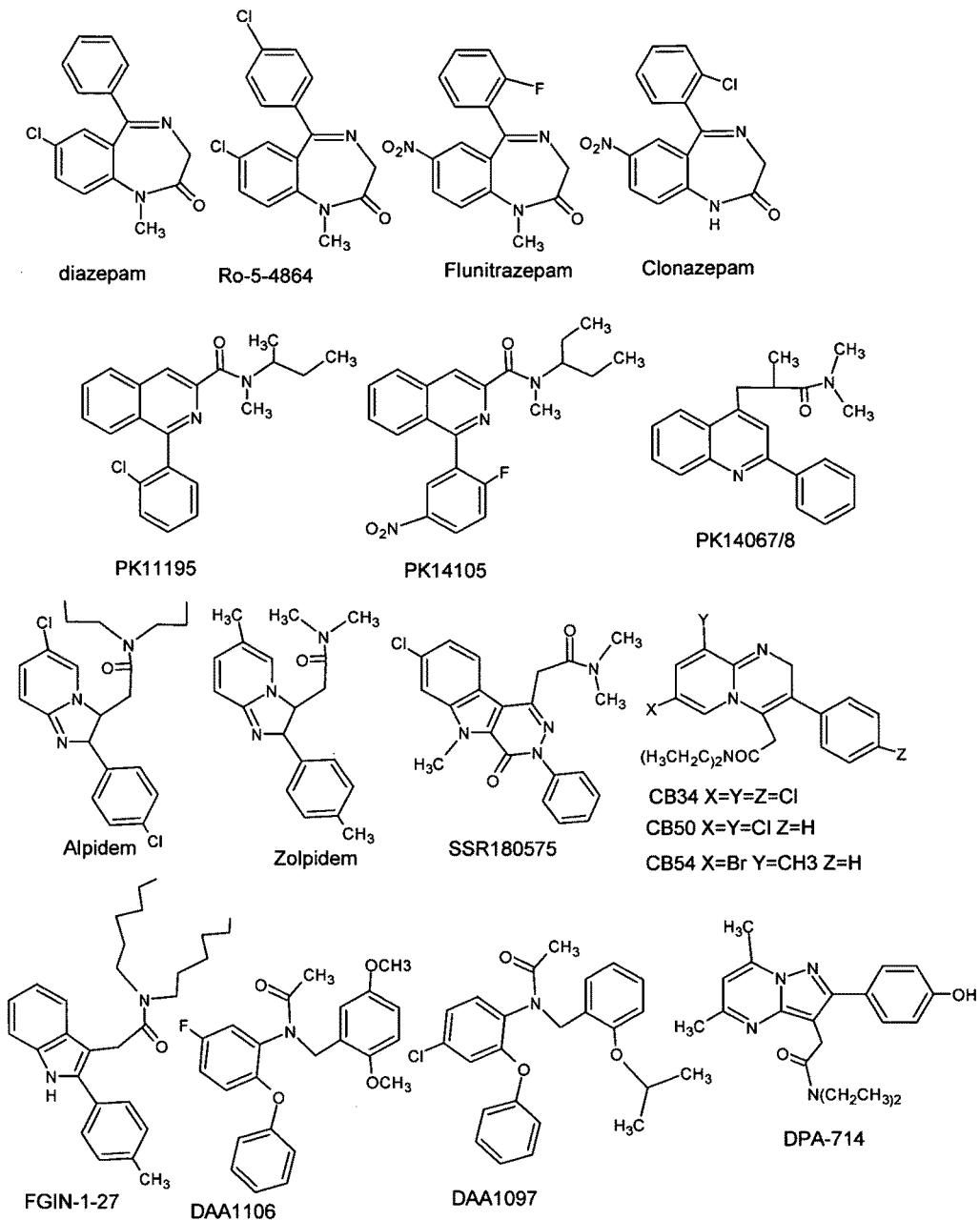
FIG. 3 presents the 2-D chemical structures of exemplary synthetic TSPO ligands.

The chemical structures of exemplary TSPO receptor ligands are presented in FIG. 3. Analyzing the structural features of these compounds show that all share a common structural motif of two adjacent rings wherein each ring may be either aromatic (e.g., phenyl) or alicyclic and at least one of the rings comprises between 1-2 nitrogen atoms. In most structures, a phenyl ring is attached to a nitrogen-containing heterocyclic ring via a single covalent bond. Some other common structural features can be identified also for the substituents of the rings.

Thus, according to some embodiments, TSPO receptor ligands that are suitable for use in the various aspects of the present invention include, but are not limited to, TSPO receptor ligands having the general formula V:

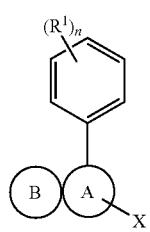

Formula V including pharmaceutically acceptable salts thereof, wherein:

A is selected from the group consisting of a substituted or unsubstituted five- or six-membered nitrogen-containing heteroalicyclic ring and a substituted or unsubstituted five- or six-membered nitrogen-containing heteroaryl ring; whereas A is linked to the benzene ring via a single covalent bond and the ring contains 1, 2 or 3 nitrogen atoms;

B is a monocyclic or bicyclic ring selected from the group consisting of a substituted or unsubstituted (C5-C6) cycloalkyl ring, a substituted or unsubstituted (C5-C6) heteroalicyclic ring, a substituted or unsubstituted (C5-C6) aryl ring, a substituted or unsubstituted (C5-C6) heteroaryl ring or a combination thereof;

X is —$R^2$—C(=O)—$NR^3R^4$ wherein $R^2$ is absent or is a substituted or unsubstituted C1-C3 alkyl;

$R^3$ and $R^4$ are each independently selected from the group consisting of hydrogen, a substituted or unsubstituted alkyl, a substituted or unsubstituted alkenyl, a substituted or unsubstituted alkynyl, a substituted or unsubstituted cycloalkyl and a substituted or unsubstituted aryl;

$R^1$ is selected from the group consisting of a C1-C3 alkyl, halide, hydroxy, alkoxy, carbonyl, oxo, thiocarbonyl, sulfinyl, sulfonyl, cyano, nitro and —$NR^5R^6$ wherein $R^5$ and $R^6$ are each independently selected from the group consisting of hydrogen and linear or branched alkyl, n is an integer from 1 to 5; and wherein when A or B are a substituted ring, the substituent is selected from the group consisting of an electronegative group, oxo, thioxo, halide, trihalomethyl, hydroxy, alkoxy, thiohydroxy, thioalkoxy, cyano, nitro, carbonyl, thiocarbonyl, C-carboxylate, O-carboxylate, O-carbamate, N-carbamate, O-thiocarbamate, N-thiocarbamate, sulfinyl, sulfonyl, C-amido, N-amido, amino and —$NR^5R^6$ as defined above.

As used herein, the phrase "electronegative group" describes a chemical moiety or atom which, when bound to another chemical moiety or atom, has at least a partial electronegative charge.

In one embodiment, at least one of the A or B rings is a substituted ring, substituted by an electronegative group. The electronegative group is preferably a oxo, thioxo, halide, hydroxy, cyano or nitro group. In one embodiment, the A ring is substituted by either oxo or thioxo.

It will be appreciated by one of skilled in the art that the feasibility of each of the variables (denoted as A, B, X and $R^1$-$R^9$) to be located at the indicated positions depends on the valency and chemical compatibility of the substituent, the substituted position and other substituents. Hence, the present embodiments are aimed at encompassing all the feasible substituents for any position.

The term "monocyclic ring" refers to a ring which is not part of a polycyclic ring system.

The term "bicyclic ring" refers to two fused rings wherein the two ring shares at least two atoms.

The term "alkyl", as used herein, describes a saturated aliphatic hydrocarbon including straight chain and branched chain groups. In some embodiments, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. In some embodiments, the alkyl is a lower alkyl having 1 to 3 carbon atoms. The alkyl group may be substituted or unsubstituted, as indicated herein. The term alkenyl, as used herein, describes an alkyl, as defined herein, which contains a carbon-to-carbon double bond.

The term alkynyl, as used herein, describes an alkyl, as defined herein, which contains carbon-to-carbon triple bond.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted, as indicated herein.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted, as indicated herein.

The term "carbonyl" or "carbonate" as used herein, describes a —C(=O)—R' group, with R' being hydrogen, alkyl, cycloalkyl or aryl, as defined herein.

The term "thiocarbonyl" or "carbonate" as used herein, describes a —C(=S)—R' group, with R' being hydrogen, alkyl, cycloalkyl or aryl, as defined herein.

The term "aldehyde" describes a carbonyl group in which R' is hydrogen.

The term "alkoxy" describes both an —O-alkyl and an —O-cycloalkyl group, as defined herein.

The term "aryloxy" describes an —O-aryl, as defined herein.

The term "C-carboxylate" describes a —C(=O)—OR' group, where R' is as defined herein.

The term "O-carboxylate" describes a —OC(=O)R' group, where R' is as defined herein.

The terms "C-carboxylate" and "O-carboxylate" are referred to herein collectively as "carboxy".

Each of the alkyl, cycloalkyl and aryl groups in the general formulas herein may be substituted by one or more substituents, whereby each substituent group can independently be, for example, alkyl, cycloalkyl, alkoxy, aryl and aryloxy, carbonyl, aldehyde and carboxy, depending on the substituted group and its position in the molecule.

Other substituents, such as heteroaryl, heteroalicyclic, amine, halide, sulfonate, sulfoxide, phosphonate, hydroxy, thiohydroxy, thioalkoxy, thioaryloxy, cyano, nitro, azo, isocyanate, sulfonamide, thiocarbonyl, acyl halide, C-carboxylate, O-carboxylate, N-thiocarbamate, O-thiocarbamate, urea, thiourea, N-carbamate, O-carbamate, C-amide, N-amide, guanyl, guanidine, silyl, and hydrazine, are also encompassed herein, as long as the functionality of the compound as a TSPO ligand is maintained. As discussed hereinabove, such a functionality can be determined by binding affinity assays known in the art.

The term "halide" or "halo" describes fluorine, chlorine, bromine or iodine.

The term "haloalkyl" describes an alkyl group as defined herein, further substituted by one or more halide.

The term "trihalomethyl" describes a methyl group substituted by three halides with the halide being as defined herein.

The term "S-sulfonamide" describes a —S(=O)₂—NR'R" group, with R' as defined herein and R" being as defined herein for R'.

The term "N-sulfonamide" describes an R'S(=O)₂NR"— group, where R' and R" are as defined herein.

The terms "S-sulfonamide" and "N-sulfonamide" are collectively referred to herein as sulfonamide.

The term "thiocarbonyl" as used herein, describes a —C(=S)—R' group, with R' as defined herein.

The term "carbonyl" as used herein, describes a —C(=O)—R' group, with R' as defined herein.

The term "hydroxyl" or "hydroxy" describes a —OH group.

The term "thiohydroxy" or "thiol" describes a —SH group.

The term "thioalkoxy" describes both an —S-alkyl group, and a —S-cycloalkyl group, as defined herein.

The term "thioaryloxy" describes both an —S-aryl and a —S-heteroaryl group, as defined herein.

The term "oxo" describes a =O group

The term "thioxo" describes a =S group

The term "sulfoxide" describes a —S(=O)R' group with R' being hydrogen, alkyl, cycloalkyl or aryl, as defined herein.

The term "phosphonate" describes a —P(=O)(OR')(OR") group, with R' and R" as defined herein.

The term "sulfonate" describes a —S(=O)₂—R' group, where R' is as defined herein.

The term "cyano" describes a —C≡N group.

The term "isocyanate" describes an —N=C=O group.

The term "nitro" describes an —NO₂ group.

The term "acyl halide" describes a —(C=O)R"" group wherein R"" is halide, as defined hereinabove.

The term "azo" or "diazo" describes an —N=NR' group, with R' as defined hereinabove.

The term "C-thiocarboxylate" describes a —C(=S)—OR' group, where R' is as defined herein.

The term "C-carboxylate" describes a —C(=O)—OR' group, where R' is as defined herein.

The term "O-thiocarboxylate" describes a —OC(=S)R' group, where R' is as defined herein.

The term "N-carbamate" describes an R"OC(=O)—NR'— group, with R' and R" as defined herein.

The term "O-carbamate" describes an —OC(=O)—NR'R" group, with R' and R" as defined herein.

The term "O-thiocarbamate" describes a —OC(=S)—NR'R" group, with R' and R" as defined herein.

The term "N-thiocarbamate" describes an R"OC(=S)NR'— group, with R' and R" as defined herein.

The term "S-dithiocarbamate" describes a —SC(=S)—NR'R" group, with R' and R" as defined herein.

The term "N-dithiocarbamate" describes an R"SC(=S)NR'— group, with R' and R" as defined herein.

The term "urea", which is also referred to as "ureido", describes a —NR'C(=O)—NR"R'" group, where R' and R" are as defined herein and R'" is as defined herein for R' and R".

The term "thiourea", which is also referred to as "thioureido", describes a —NR'—C(=S)—NR"R'" group, with R', R" and R'" as defined herein.

The term "C-amide" describes a —C(=O)—NR'R" group, where R' and R" are as defined herein.

The term "N-amide" describes a R'C(=O)—NR"— group, where R' and R" are as defined herein.

The terms "N-amide" and "C-amide" are collectively referred to herein as amide.

The term "guanyl" describes a R'R"NC(=N)— group, where R' and R" are as defined herein.

The term "guanidine" describes a —R'NC(=N)—NR"R'" group, where R', R" and R'" are as defined herein.

The term "hydrazine" describes a —NR'—NR"R'" group, with R', R", and R'" as defined herein.

The term "amine" describes a —NR'R" group, with R' and R" as described herein.

The term "silyl" describes a —SiR'R"R'" group, whereby each of R', R" and R'" are as defined herein.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

The term "heteroalicyclic" or "heterocyclyl" describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofurane, tetrahydropyrane, morpholino and the like.

The configuration of the chiral carbon atoms that may be present in the TSPO receptor ligand can be R configuration or S configuration.

Herein throughout, the term "agent" encompasses a TSPO receptor ligand, as described herein. In some embodiments, the term "agent" relates to diazepam, as described herein.

The term "additional agent" is used to describe agents other then a TSPO receptor ligand and/or diazepam, as described herein.

In some embodiments, the agent described herein (e.g., a diazepam) is preferably selected as being capable of suppressing an innate immune activity in a subject using the article of manufacturing.

The agent (e.g., diazepam) is further preferably selected as being capable of inhibiting inflammation in a subject.

The present embodiments further encompass pharmaceutically acceptable salts of any of the agents described herein.

The phrase "pharmaceutically acceptable salt" describes a charged species of the parent compound and its counter ion, which is typically used to modify the solubility characteristics of the parent compound and/or to reduce any significant irritation to an organism by the parent compound, while not abrogating the biological activity and properties of the administered compound. Examples, without limitation, include an acid additional salt of an amine group.

The present invention further encompasses prodrugs, solvates and hydrates of the agents described herein.

As used herein, the term "prodrug" refers to a molecule, which is converted into the active compound (the active parent drug) in vivo. Prodrugs are typically useful for facilitating the administration of the parent drug. They may, for instance, be bioavailable by oral administration whereas the parent drug is not. The prodrug may also have improved solubility as compared with the parent drug in pharmaceutical compositions. Prodrugs are also often used to achieve a sustained release of the active compound in vivo. An example, without limitation, of a prodrug would be a compound, having one or more carboxylic acid moieties, which is administered as an ester (the "prodrug"). Such a prodrug is hydrolysed in vivo, to thereby provide the free compound (the parent drug). The selected ester may affect both the solubility characteristics and the hydrolysis rate of the prodrug.

The term "solvate" refers to a complex of variable stoichiometry (e.g., di-, tri-, tetra-, penta-, hexa-, and so on), which is formed by a solute (the agent described herein) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

According to one aspect of embodiments of the present invention there is provided an article of manufacturing which comprises tobacco and a tobacco packaging material, wherein at least a portion of the tobacco and/or the tobacco packaging material comprises an agent, namely, a TSPO receptor ligand, as described herein.

According to another aspect of embodiments of the present invention there is provided an article of manufacturing which comprises tobacco and an agent as described herein being incorporated in at least a portion of the tobacco.

According to another aspect of embodiments of the present invention there is provided an article of manufacturing which comprises a tobacco packaging material and an agent as described herein being incorporated in at least a portion of the tobacco packaging material.

The term "agent" refers to any of the TSPO receptor ligands, (e.g., diazepam) described herein.

In one embodiment relating to the articles of manufacturing described herein, that portion of tobacco and/or the tobacco packaging material which comprises the agent is in contact with an aerodigestive tract of a subject using the article of manufacturing.

As used herein the term "tobacco" refers to any tobacco species (e.g., crude or extract) which is compatible with human use. The agent can be incorporated in the tobacco (or a portion thereof), by mixing, dipping, spraying, coating, or any other chemical or physical attachment.

On top of tobacco, the present embodiments also envisage the use of the agents described herein (in line with the above described aspects) with other smoked, dipped, chewed, snuff or snused herbs, compatible with human consumption and which cause a damage similar to that damage induced by tobacco, as detailed hereinunder.

As used herein, the phrase "tobacco packaging material" refers to any auxiliary means which packages the tobacco or facilitates its consumption (carrier). Examples include, but are not limited to, rolling paper, snus bags, filter paper, tin sheets and the like.

Thus, for example, the agent may be impregnated in (attached to, absorbed in, coated with) a filter paper which comes in direct contact with the aerodigestive tract.

The articles of manufacturing described herein can therefore be, for example, tobacco products such as smoking products (e.g., cigarettes, non-filter cigarettes, cigars, and other tobacco products as described hereinabove) or products used in the manufacturing of tobacco products (e.g., cigarette filters, rolling papers and the like).

Figure 2:
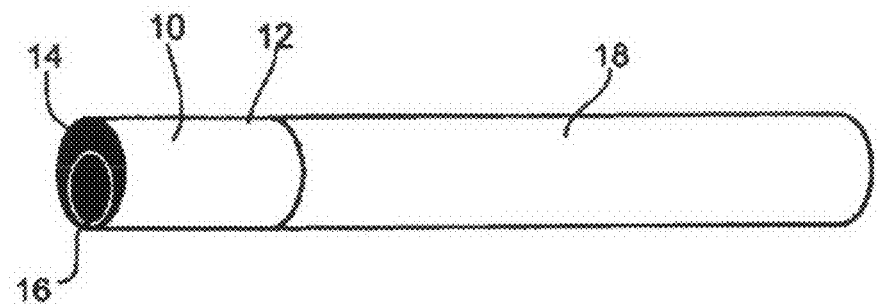
FIG. 2 is schematic diagram depicting the construction of a filter paper impregnated with agents according to embodiments of the present invention.

FIG. 2 illustrates a cigarette filter configuration which is referred to hereinunder as a cigarette filter 10. Cigarette filter 10 is constructed of a paper lining 12 and a filter core 14 which is composed of glass fiber and is positioned adjacent to a tobacco filling 18. To enable effective delivery the agent of the present invention can be disposed as an aqueous emulsion within a rupturable capsule 16 positioned at the front of filter core 14. Alternatively, the agent may also be dispersed, impregnated in tobacco filling 18 or provided throughout in droplets or beadlets through the employment of gelatin or other colloidal materials, so that the agent can be easily entrained by the smoke passing through filter core 14. Such filters have been previously described, for example, in U.S. Pat. Nos. 3,667,478 and 3,339,558, the teachings of which are herein incorporated by reference as if fully set forth herein.

Alternatively, the rolling paper may be treated with the agent such that the agent is confined to that region of the paper which comes in contact with the aerodigestive tract (say about 1 cm margins).

Such tobacco filters can be used as follows: prior to lighting up, pressure is applied to rupturable capsule 16, so that the released agents are dispersed within filter core 14, whereby the agent is accessible to the cigarette smoke passing through.

Thus, in some embodiments of the present invention, the articles of manufacturing described herein are preferably designed and configured so as to enable physico-chemical interaction between the agent and the tobacco smoke. In some embodiments, the articles of manufacturing are designed and configured so as to enable release of the agent therefrom when in use by a subject.

As used herein, "aerodigestive tract" refers to saliva-lined tissues such as the lips, mouth, buccal cavity, tongue, oropharynx, throat, larynx, esophagus, upper digestive tract, saliva glands, saliva, as well as the similar mucous-lined tissues of the respiratory tract, such as the respiratory mucosa, alveoli, trachea, and lungs.

Further according to the present embodiments, there is provided an article of manufacturing, being a filter, which comprises an agent as described herein and which is designed and configured so as to enable release of the agent therefrom when in use by a subject.

In some embodiments, the filter is designed and configured as a tobacco smoke filter (see, for example, FIG. 2). Such a filter can be incorporated into "filter-tip cigarettes", cigarette holders, gas-masks, protective face-masks, and air-conditioning unit filters.

In some embodiments, any of the articles of manufacturing described herein further comprises an additional agent that is capable of reducing or preventing a tobacco-associated damage, as described herein, in a subject using the article of manufacturing.

The additional agent can be incorporated (or impregnated) in the tobacco or the tobacco packaging material or in the above-described filter.

Since tobacco-associated damage often involves oxidative damage, exemplary such additional agents are antioxidants. In one embodiment, the antioxidant is glutathione (GSH).

Glutathione (GSH) is a tripeptide (L-c-glutamyl-L-cysteinyl-glycine) containing a thiol group. GSH is an important protective antioxidant against free radicals and other oxidants, and has been implicated in immune modulation and inflammatory responses. Glutathione exists in reduced (GSH) and oxidized (GSSG) states. In the reduced state, the thiol group of cysteine is able to donate a reducing equivalent ($H^+ + e^-$) to other unstable molecules, such as reactive oxygen species. In donating an electron, glutathione itself becomes reactive, but readily reacts with another reactive glutathione to form glutathione disulfide (GSSG). GSH protects cells against CS-born aldehydes, which are known to mediate CS damage.

Addition of GSH to the cultured medium inhibited the lethal synergistic effect and increased the survival rate, while there was no additional protection following CS exposure alone (see, PCT/IL2008/000628). These results demonstrate that aldehydes lethal effect can be accelerate by saliva and CS exposure. It can be assumed that the lack of GSH protection following CS alone is a result of cell-type specific that dose not susceptible to low active-aldehydes.

The possible protection ability of GSH is also demonstrated by the ability to prevent the rapid downregulation of p53 following CS and saliva exposure. This effect may be attributes to the decrease of oxidized thiols by GSH, resulted in less p53 aggregation and subsequent degradation.

The antioxidant can further include a cyanide ($CN^-$) chelator, which can be used to treat tobacco-associated loss of OPO activity. An example of such a chelator is OH—CO, also known as the non-cyanide-bound form of cyanocobalamin, hydroxocobalamin or vitamin B12a. Other examples include, but are not limited to, epselen, vitamins A, C and E, selenium compounds, flavenoids, quinones (e.g., Q10, Q9), retinoids and carotenoids.

Preferably, the $CN^-$ chelator (e.g., OH—CO) is utilized in a manner which enables establishment of a concentration of 0.5-2 mM, preferably 1 mM in body fluids, such as saliva.

Cyanide chelators can be effectively employed to prevent or reduce tobacco-associated damage in the aerodigestive tract since they act to sequester cyanide which is injurious to OPO.

Other antioxidants include redox-active metal ion chelators, e.g., redox-active iron chelators (also referred to herein as iron chelating agents). Examples include deferoxamine, and zinc-desferrioxamine.

The chelating agent deferoxamine is also known as DES, desferal and desferrioxamine.

Redox-active metal ion chelators are used in a manner which enables establishment of about 1 mM concentration in body fluids (e.g., saliva). Preferably, deferoxamine is administered in a manner which enables establishment of a concentration of about 1 mM, more preferably about 5 mM in body fluids. More preferably, a mixture of deferoxamine and GSH is used in a ratio of about 1:1, preferably 5:1, respectively. When used in combination, deferoxamine and GSH body fluid concentrations of about 1 mM each are desirable although a deferoxamine concentration of 5 mM and a GSH concentration of 1 mM are also therapeutically effective.

The articles of manufacturing described herein can further comprise at least one flavorant such as, but not limited to, wintergreen oil, oregano oil, bay leaf oil, peppermint oil, spearmint oil, clove oil, sage oil, sassafras oil, lemon oil, orange oil, anise oil, benzaldehyde, bitter almond oil, camphor, cedar leaf oil, marjoram oil, citronella oil, lavender oil, mustard oil, pine oil, pine needle oil, rosemary oil, thyme oil, and cinnamon leaf oil.

Any of the agents and additional agents described herein may be introduced to the article of manufacturing as described above (e.g., snuff), such as in the form a dry powder, either as a mixture of antioxidants, or as a complex in protective liposomes, nanospheres or other acceptable delivery vehicles. This powder may be added in the final process of manufacturing and may also contain suitable flavors or fragrances as not infrequently used in this industry.

As discussed hereinabove and is exemplified in the Examples section that follows, the agents described herein are highly efficient in reducing or preventing oxidative stress related damages, such as damages caused by tobacco (e.g., by cigarette smoke).

Thus, according to another aspect of embodiments of the present invention there is provided a method of treating or preventing a physiological disorder associated with oxidative stress, in a subject in need thereof, which is effected by administering to the subject a therapeutically effective amount of a TSPO receptor ligand, as described herein.

Accordingly, according to another aspect of embodiments of the present invention, there is provided use of any of the agents described herein in the manufacture of a medicament for treating or preventing a physiological disorder caused by oxidative stress. In some embodiments, administering the agents described herein is effected via, for example oral, rectal, transmucosal, transdermal, topical, intestinal or parenteral delivery, including intramuscular, subcutaneous and intramedullary injections as well as intrathecal, direct intraventricular, intravenous, intraperitoneal, intranasal, or intraocular injections.

As used herein, the phrase "oxidative stress" describes reversible and nonreversible damage to cellular or macromolecular components in a body of a subject (e.g., a mammalian subject such as human), which is caused by reactive forms of oxygen (called reactive oxygen species (ROS). The damage can result, for example, in cell death, inhibition or decrease in cell growth and/or proliferation, biological pathway inhibition or malfunction, and the like.

The phrase "physiological disorder associated with oxidative stress" describes a pathological condition characterized by an imbalance between production (increased) and elimination (reduced) of ROS.

Exemplary physiological disorders associated with oxidative stress include, but are not limited to, neurodegenerative disorders, amyotrophic lateral sclerosis, Huntington's disease, Parkinson's disease, Alzheimer's disease, Creutzfeldt-Jakob disease, multiple sclerosis, spongiform encephalopathies, degenerative diseases of the basal ganglia, motoneuron diseases and memory loss; Diabetes, insulin resistance syndrome, retinopathy, blindness, Cataract formation, an infectious disease, a neurological dysfunction following cardiac surgery, a cardiovascular disease, stroke, atherosclerosis, hypertension, coronary heart disease and restenosis; cerebral ischemia, cancer, prostate cancer, bladder cancer, arthritis, chronic obstructive pulmonary disease, paralysis, AIDS, alcohol addiction, periodontitis, inflammatory bowel disease, colorectal disease, chronic kidney disease, alcoholic liver disease, a mitochondrial disease, a metabolic disease, a skin disease, a skin damage, a radiation damage, a damage caused by tobacco use, an excessive angiogenesis, an insufficient angiogenesis, a hearing loss, a collateral damage of chemotherapy and mucositis.

In some embodiments, physiological disorders associated with oxidative stress include, but are not limited to, spongiform encephalopathies, motoneuron diseases and memory loss; Diabetes, insulin resistance syndrome, retinopathy, blindness, Cataract formation, an infectious disease, a neurological dysfunction following cardiac surgery, stroke, hypertension; cerebral ischemia, chronic obstructive pulmonary disease, paralysis, AIDS, periodontitis, inflammatory bowel disease, colorectal disease, chronic kidney disease, alcoholic liver disease, a mitochondrial disease, a metabolic disease, a damage caused by tobacco consumption, an excessive angiogenesis, an insufficient angiogenesis, a hearing loss, a collateral damage of chemotherapy and mucositis.

In some embodiments, physiological disorders associated with oxidative stress include diseases and disorders that involve a tobacco-associated damage.

According to yet another aspect of embodiments of the present invention there is provided a method of treating or preventing a tobacco-associated damage in a subject in need thereof, which is effected by administering to the subject a therapeutically effective amount of a TSPO receptor ligand, as described herein.

Accordingly, according to another aspect of embodiments of the present invention, there is provided use of any of the agents described herein in the manufacture of a medicament for treating or preventing a tobacco-associated damage.

Subject treatable by the method described herein include tobacco consumers, as well as secondary tobacco consumers (non-smokers that are exposed to tobacco smoke).

As used herein, the phrase "tobacco-associated damage" described cellular or macromolecular damage which is induced or exacerbated by exposure to tobacco consumption. The phrase "tobacco consumption" includes, for example, tobacco smoking (including primary and secondary smoking), chewing, sniffing, and the like, as described hereinabove.

As further discussed hereinabove, the tobacco-associated damage can be a cellular damage, resulting in, for example, cell death, cell malfunction, cell mutation, and the like; or a macromolecular damage, resulting in modification of macromolecules such as lipids, DNA and proteins.

As further discussed hereinabove, tobacco-associated damage typically involves ROS and therefore often involves oxidative damage of cells and cell components. Tobacco consumption often results in protein carbonylation in the plasma.

Being in direct contact with the aerodigestive tract, tobacco consumption results in tobacco-associated damage to mucosal tissues, particularly saliva-lined tissues such as the lips, mouth, buccal cavity, tongue, oropharynx, throat, larynx, esophagus, upper digestive tract, saliva glands, saliva, as well as the similar mucous-lined tissues of the respiratory tract, such as the respiratory mucosa, alveoli, trachea, and lungs.

Tobacco-associated damage, however, can further affect non-mucosal tissues.

As further discussed hereinabove, tobacco-associated damage is typically manifested as various diseases and disorders, including, but not limited to, cardiovascular diseases, chronic obstructive pulmonary disease, lung cancer, as well as other forms of cancer and peripheral vascular disease.

Exemplary cardiovascular diseases that are therefore treatable by the agents described herein include, but are not limited to, atherosclerosis; coronary thrombosis, which may lead to a heart attack; cerebral thrombosis, which may lead to collapse, stroke and paralysis; affected kidney arteries, which result in high blood pressure or kidney failure; and blockage of the vascular supply to the legs, which may lead to gangrene and amputation.

Exemplary cancers that are treatable by the agents described herein, in addition to lung cancer, include, but are not limited to, mouth, pharynx, and esophagus cancer, and oral squamous cell carcinoma. Other types of cancers include bladder cancer, cancer of the kidneys, cancer of the pancreas and cervical cancer.

Exemplary chronic obstructive pulmonary diseases (COPD) that are treatable by the agents described herein include, but are not limited to, emphysema and chronic bronchitis. Severe asthma can be deteriorated as a result of exposure to tobacco smoke, and moreover, such am exposure often contradicts the effect of asthma medications.

Other damages associated with tobacco consumption, which are treatable by the agents described herein include, for example, hypertension, fertility problems, retinoic disorders such as macular degeneration and cataracts, ulcers, periodontal diseases, impotence, Diabetes type 2, Back pain, skin ailments such as premature ageing and wrinkling, osteoporosis, earlier menopause, and damaged and/or weakened immune system, as well as leukoplakia, halitosis, acute necrotizing ulcerative gingivitis ("trench mouth") and oral submucous fibrosis.

As used herein, the phrase "therapeutically effective amount" describes an amount of the agent utilized which will relieve to some extent one or more of the symptoms of the condition being treated or, alternatively, which will protect to some extent against potential damages that may cause this condition, as described herein.

In one embodiment, the agent is administered or otherwise utilized in the preparation of a medicament or composition as described herein, such that its concentration is within the subnanomolar ranges, as described herein.

Some of the TSPO ligands described herein (e.g., diazepam), exhibit a beneficial effect when utilized in such a low concentration, whereby at higher concentration, a reverse effect is sometimes observed.

In any of the methods and uses described herein, the agent can be utilized in combination with an additional agent. The additional agent can be, for example, an antioxidant as described herein, an agent capable of reducing or preventing a tobacco-associated damage and/or an agent suitable for use in the treatment of a disease or disorder as described herein.

In any of the methods and uses described herein, the agent can be utilized either per se or being formulated into a pharmaceutical composition which further comprises a pharmaceutically acceptable carrier.

Hence, according to still another aspect of the present invention, there are provided pharmaceutical compositions, which comprise one or more of the agents described above and a pharmaceutically acceptable carrier.

As used herein a "pharmaceutical composition" refers to a preparation of one or more of the agents described herein, with other chemical components such as pharmaceutically acceptable and suitable carriers and excipients. The purpose of a pharmaceutical composition is to facilitate administration of a compound to an organism.

Hereinafter, the phrase "pharmaceutically acceptable carrier" describes a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the agents described herein into preparations which, can be used pharmaceutically. Proper formulation is dependent upon the route of administration chosen.

According to some embodiments, the pharmaceutical composition is formulated as a solution, suspension, emulsion or gel.

According to some embodiments, the pharmaceutical composition further includes a formulating agent selected from the group consisting of a suspending agent, a stabilizing agent and a dispersing agent.

For injection, the agents described herein may be formulated in aqueous solutions, preferably in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

For oral administration, the agents described herein can be formulated readily by combining the agents with pharmaceutically acceptable carriers well known in the art. Such carriers enable the agents described herein to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active agent doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the agent (s) may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the agents described herein are conveniently delivered in the form of an aerosol spray presentation (which typically includes powdered, liquified and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the agents and a suitable powder base such as, but not limited to, lactose or starch.

The agents described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the agents described herein in water-soluble form. Additionally, suspensions of the agents may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the agents to allow for the preparation of highly concentrated solutions.

Alternatively, the agents may be in powder form for constitution with a suitable vehicle, e.g., sterile, pyrogen-free water, before use.

The agents described herein may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of an agent as described herein effective to prevent, alleviate or ameliorate symptoms of a physiological disorder associated with oxidative stress (such as tobacco-associated damage) or prolong the survival of the subject being treated.

Determination of a therapeutically effective amount is well within the capability of those skilled in the art, especially in light of the detailed disclosure provided herein.

For any agent utilized in the methods and uses of the invention, the therapeutically effective amount or dose can be estimated initially from activity assays in animals. For example, a dose can be formulated in animal models to achieve a circulating concentration range that includes the $IC_{50}$ as determined by activity assays (e.g., the concentration of the test agent, which achieves a half-maximal reduction in cell death upon exposure to cigarette smoke). Such information can be used to more accurately determine useful doses in humans.

Toxicity and therapeutic efficacy of the agents described herein can be determined by standard pharmaceutical procedures in experimental animals, e.g., by determining the $EC_{50}$, the $IC_{50}$ and the $LD_{50}$ (lethal dose causing death in 50% of the tested animals) for a subject compound. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Depending on the severity and responsiveness of the condition to be treated, dosing can also be a single administration of a slow release composition described hereinabove, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present embodiments may, if desired, be presented in a pack or dispenser device, such as an FDA (the U.S. Food and Drug Administration) approved kit, which may contain one or more unit dosage forms containing the active agent. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising an agent as described herein, formulated in a compatible pharmaceutical carrier may also be prepared, placed in an appropriate container, and labeled for treatment of an indicated condition, as is detailed hereinabove.

Thus, according to an embodiment of the present invention, the pharmaceutical composition is packaged in a packaging material and identified in print, in or on the packaging material, for use in the treatment of a physiological disorder associated with oxidative stress, as described herein.

According to another embodiment, the pharmaceutical composition is packaged in a packaging material and identified in print, in or on the packaging material, for use in the treatment or prevention of a tobacco-associated damage, as described herein.

In some embodiments, the pharmaceutical composition further comprises an additional agent. The additional agent can be, for example, an antioxidant as described herein, an agent capable of reducing or preventing a tobacco-associated damage and/or an agent suitable for use in the treatment of the indicated disease or disorder as described herein. An exemplary antioxidant is glutathione (GSH).

The pharmaceutical composition described herein can be utilized, for example, as a food additive or a nutritional additive. Such a composition is preferably formulated for oral administration and can further comprise other food or nutritional supplements such as vitamins and the like.

Since it has been shown herein that the level of TSPO receptor is decreased upon exposure to cigarette smoke, and that the agents described herein are used in a manner that prevents or reduces damages associated with such a decrease, the agents described herein can be utilized as protecting agents.

The compositions described herein can therefore be used to protect against tobacco-associated damage, as described herein, or against any other physiological disorder associated with oxidative stress, as described herein.

It is noted in this respect that any of the articles, methods, uses and compositions described herein can be routinely utilized in order to protect against, and thus prevent, tobacco-associated damage, as described herein, or any other physiological disorder associated with oxidative stress, as described herein.

According to another aspect of the present invention there is provided an oral composition which comprises an agent as described herein. The oral composition can be in the form of a toothpaste, powder, liquid dentifrice, mouthwash, denture cleanser, chewing gum, lozenge, paste, gel or candy and can further comprise at least one flavorant such as wintergreen oil, oregano oil, bay leaf oil, peppermint oil, spearmint oil, clove oil, sage oil, sassafras oil, lemon oil, orange oil, anise oil, benzaldehyde, bitter almond oil, camphor, cedar leaf oil, marjoram oil, citronella oil, lavender oil, mustard oil, pine oil, pine needle oil, rosemary oil, thyme oil, and cinnamon leaf oil.

Exemplary chewing gum compositions are described in U.S. Pat. No. 5,922,346, which is incorporated by reference as if fully set forth herein.

The chewing gums, gels or pastes of these embodiments may include bicarbonates with thickening agents in a concentration from 0.5% to 5.0% by weight. Exemplary thickeners with bicarbonate and zinc salts include, but are not limited to, chicle, xanthan, arabic, karaya or tragacanth gums. Alginates, carrageenans and cellulose derivatives such as sodium carboxymethyl, methyl, or hydroxy ethyl compounds are appropriate for the intended preparations; surfactants and abrasives may also be included. Alcohols will otherwise be avoided for their known risk factor for oral cancers. In order to decrease dental cavities and add flavor, without using metabolizable sugars, sweetening agents as saccharin, sodium cyclamate, sorbitol, aspartame and others may be used in concentrations from 0.005% to 5.0% by weight of the total composition. Xylitol has been shown to prevent dental caries and decrease gum disease, in part by reducing the putative oral bacteria, especially *Streptococcus* mutants.

Gels and dentifrices may contain fluoride anticaries compounds. These fluoride compounds, such as salts of sodium, potassium, calcium, magnesium, stannous and others have been known to protect teeth from developing cavities. Fluorides may be present in various amounts in the gels, pastes, gums or lozenges ranging from 0.01% to 3.0% by weight, preferably from 0.05% to 2.0% by weight, most preferably from 0.1% to 1.2% by weight. These sources of stabilized fluoride are taught in U.S. Pat. No. 5,372,802.

The agents described herein can also be incorporated into additional articles. These include, for example, various medical devices for delivering the agent to or applying the agent on a desired bodily site.

As used herein, the phrase "bodily site" includes any organ, tissue, membrane, cavity, blood vessel, tract, biological surface or muscle, which delivering thereto or applying thereon the agents described herein is beneficial.

Exemplary medical devices are those configured to deliver the agent by topical application, (e.g., an adhesive strip, a bandage, an adhesive plaster, and a skin patch).

The agents can be incorporated in the device structure by any methodology known in the art, depending on the selected nature of the device structure. For example, the agents can be entrapped within a porous matrix, swelled or soaked within a matrix, or being adhered to a matrix.

In any of the articles, compositions and devices described herein, the agent can be utilized in combination with an additional active agent, as described herein.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Experimental Methods

Materials:

Tobacco smoke was obtained from popular commercial cigarettes containing 14 mg of tar and 0.9 mg of nicotine ('Time' cigarettes, Dubek Ltd., Tel Aviv, Israel), and was generated as described hereinbelow.

Human non-small cell lung cancer NCI-H1299 cells were used as described by the American Type Culture Collection.

Culture medium included DMEM with L-glutamine, supplemented with fetal bovine serum (10%) and penicillin-streptomycin solution (1%).

The cells were grown at 37° C. in 5% $CO_2$.

Culture medium ingredients were supplied by Beit HaEmek-Biological Industries, Israel.

Diazepam and clonazepam, were purchased from Sigma-Aldrich, Israel.

$[^3H]$PK 11195 was obtained from New England Nuclear (Boston, Mass.).

Unlabeled PK 11195 was purchased from Sigma-Aldrich Israel.

Cell Death Kit (Cell Death Detection ELISA™ KIT) was purchased from Roche diagnostics, Germany.

Cancer Cell Lines:

SCC-25 and SCC-15 cell lines (human oral squamous cell carcinoma cells from the American Type Culture Collection, Rockville, Md., USA: SCC-15 ATCC #CRL-1623; and SCC-25 ATCC #CRL-1628) were grown in 90% DMEM-Ham's F-12 media. Cultures medium included 10% heat-inactivated FBS, 2.5 mM L-glutamine, penicillin-streptomycin solution (10,000 units/ml penicillin sodium salt and 10 mg/ml streptomycin sulfate) (1% v/v). Cells were grown at 37° C. in 95% air and 5% $CO_2$.

Saliva Collection:

Whole saliva was collected from healthy volunteers (20-60 years) under non-stimulatory condition, at least 1 hour after last eating, between 8:00-12:00 AM. The volunteers were asked to generate saliva in their mouths and to spit it into a wide test tube for no more then 20 minute. The obtained whole saliva was centrifuged at 1200×g for 15 minutes to remove cell debris and palate cells, and the supernatant was used for further applications.

Study Design:

Experiments were conducted using H1299 human lung cancer cells.

Four control groups, not exposed to tobacco smoke (referred to herein as TS or alternatively, as CS, standing for "cigarette smoke") were compared to four study groups (similar groups which were also exposed to CS), as detailed hereinafter. The four control groups included the following: a group where the cells were incubated in medium alone and exposed to air (M), a group where the cells were incubated in medium supplemented with whole saliva and exposed to air (M+saliva), a group where the cells where incubated in medium and exposed to CS (M+CS) and a group where the cells were incubated in medium supplemented with saliva and exposed to CS (M+saliva+CS). Accordingly, the four study groups were exposed to the same conditions and further exposed to either diazepam or clonazepam, at the indicated concentration.

Exposure to Cigarette Smoke (CS) with/without Saliva:

During smoke exposure, the cells were put into a smoking sealed chamber (33.5 $cm^3$) with CS pressure of 0.3 Bar. Control cells were subjected to the same procedures, but exposed only to fresh air. Cells were exposed to CS for one "puff" every 20 minutes for a 2 hours (120 minutes) period (unless indicated otherwise). Cells exposed to air served as control. Cells were used when it becomes confluent and the medium (with/without saliva) volume was compatibly to the dish in use.

Whole Cell Extract Preparation from Saliva and SCC-25, SCC-15 and H1299 Cell Lines:

Saliva samples were centrifuged (800 g, 10 minutes, 4° C.) and the pellet was suspended in a lysis buffer containing 1 tablet of protease inhibitor, 0.1% SDS, PBS (pH=7.4) and 1% Triton X-100. After 30 minutes of incubation at room temperature, samples were centrifuged (10,000 g, 10 minutes, 4° C.) and Protein concentration was measured by the Bradford method (1976) [Bradford M. M. 1976. *Anal. Biochem.* 72:248-254], using BSA as a standard.

Cells medium, after CS exposure, were removed and the cultured SCC-25, SCC-15 or H1299 cells were collected by scraping. Samples were centrifuged at 1200×g for 10 minutes. The cell pellets were lysed with 50-150 µL, lysis buffer containing 1% Triton X-100, 1 tablet/10 ml protease inhibitor and 0.1% SDS dissolved in PBS, pH 7.4, for 30 minutes on ice. Cell extracts were thereafter centrifuged at 12,000×g for 10 minutes at 4° C. The supernatants were transferred into 1.5 ml eppendorf tube and stored at −20° C. until used. Protein concentration was measured by the Bradford method (1976) [Bradford M. M. 1976. *Anal. Biochem.* 72:248-254], using BSA as a standard.

Western Blot Analyses:

Crude lysates from saliva were prepared in 2× sample buffer (0.125 M Tris-Cl (pH=6.8), 20% glycerol, 4% (w/v) SDS, 0.14 M β mercaptoethanol, 0.0005% (w/v) bromophenol blue). The samples were boiled for 7 minutes (100° C.), and then cooled on ice, loaded onto the 12% SDS-polyacrylamide gel (5-20 µg protein/lane) for SDS-polyacrylamide gel electrophoresis (100V), and blotted onto nitrocellulose membranes for 90 minutes at 95V. Blots were blocked with 5% dried milk in a PBS-Tween solution (PBS-T, PBS containing 0.1% Tween 20) for 1 hour. After several washes in PBS-T, the membrane was incubated with three primary antibodies, a laboratory self-produced primary anti-TSPO antibody (rabbit anti-human), a commercial primary anti-VDAC antibody (mouse anti-human) and a monoclonal anti-β-actin antibody (mouse anti human), overnight. The membrane was then washed 3 times in PBS-T followed by a 1 hour incubation with the secondary antibody (anti-rabbit and anti mouse) IgG linked to horseradish peroxidase. Binding of antibodies to the membrane was detected with an ECL-detection reagent and exposed to Kodak imaging film.

Crude lysates of SCC-25, SCC-15 or H1299 cancer cell lines, exposed to saliva, CS and CS+saliva, whereby exposure to CS was for various time lengths, were prepared, loaded onto 12% SDS-polyacrylamide gel, and blotted onto nitrocellulose membranes for 1 hour at 100 W. Blots were blocked with 5% non-fat milk in PBS-T (PBS containing 0.1% Tween 20) and then incubated for 2 hours or overnight at 4° C. with anti-human TSPO (1:1000), anti-human VDAC (1:4000), or (β-actin (1:15000). After three washes with PBS-T, the membrane was incubated with a secondary antibody (anti-rabbit IgG 1:3000, anti mouse IgG 11:5000) in PBS-T for 1 hour at room temperature. Binding of antibodies to the membrane was detected with an ECL-detection reagent and exposed to Kodak imaging film.

SCC-25 and SCC-15 Cells Survival:

Cells viability was measured at various time points by Trypan Blue exclusion test, both in exposed and control cells.

The medium covering the dish was collected and cells were trypsinized and centrifuged at 1200×g for 10 minutes. Cell pellets were re-suspended in 1 mL of medium and a sample was collect for cell counting. Cells were stained with the vital dye Trypan Blue at final concentration of 0.25% and were placed on hemocytometer. Visual counting was preformed by inverted microscope.

[$^3$H]PK 11195 Binding Assays in SCC-25, SCC-15 or H1299 Cells:

[$^3$H]PK 11195, an isoquinoline carboxamide derivative, was used for binding studies. PK 11195 is a specific TSPO receptor ligand. Cells were scraped from the culture dishes, washed with phosphate-buffered saline (PBS), and centrifuged at 1200 g for 10 minutes. Then the cell pellets were re-suspended in 1 mL of 50 mM phosphate buffer, pH 7.4, and centrifuged at 1200 g for 10 minutes. Binding assays contained 400 µL of cell membrane (0.4 mg of protein/mL) in the absence (total binding) or presence (non-specific binding) of 1 µM unlabeled PK 11195, up to a final volume of 500 µL. After incubation for 80 minutes at room temperature, samples were filtered under vacuum over Whatman GF/B filters and washed three times with phosphate buffer. Filters were placed in vials containing 4 mL of Opti-Fluor (Packard, Groningen, The Netherlands) and counted for radioactivity in a scintillation counter after 12 hours. The maximal number of binding sites (Bmax) and equilibrium dissociation constants were calculated from the saturation curve of [$^3$H] PK 11195 binding, using Scatchard analysis.

[$^3$H]PK 11195 Binding Assays in Saliva Samples:

For Binding analysis, saliva samples were thawed and immediately centrifuged (800 g, 10 minutes, 4° C.). The pellet, containing saliva cells, was suspended in ice-cold phosphate buffer saline (PBS), and then homogenized using a Polytron (setting 6) for 10 seconds. Total protein amount was determined.

Binding of [$^3$H]PK11195 to membranes of the saliva cell was conducted, as previously described (Awad and Gavish, 1987; Kelly-Hershkovitz et al., 1988; Carmel et al., 1999). The reaction mixture contained 400 µl of the homogenized samples and 25 µl of [$^3$H]PK 1195 (final concentration of 0.19-6 nM), in the absence (total binding) or in the presence (non-specific binding) of 10 µM unlabeled PK 11195. After 80 minutes of incubation at 4° C., the samples were filtered through Whatman CF/C filters using a vacuum system, washed three times with 4 ml of 5 mM ice-cold phosphate buffer and placed in vials containing 4 ml of Opti-Fluor. Radioactivity was counted after 12 hours with a liquid scintillation analyzer. Specific binding was obtained by subtracting non specific binding from total binding.

The maximal number of binding sites (Bmax) and equilibrium dissociation constants were calculated from the saturation curve of [$^3$H]PK11195 binding, using Scatchard analysis.

Protein Carbonyl Assay:

Protein carbonyl concentration was determined by enzyme-linked immunosorbent assay (ELISA), using the Zentech PC Test Kit (Zenith Technology, Dunedin, New Zealand). Briefly, protein cell extractions were allowed to react with a dinitrophenylhydrazine (DNP) solution (200 µl). The DNP-reacted proteins bound non-specifically to an ELISA plate, and the unconjugated DNP and non-protein entities were washed away. The adsorbed DNP-protein was then probed with an anti-DNP-biotin antibody, followed by a streptavidin-linked HRP probe. Then the chromatin reagent that contained peroxide was added to catalyze the oxidation of TMB. Finally, the reaction was stopped by the addition of a stopping reagent (acid, provided with the kit), and the absorbance was measured for each well at 450 nm using a spectrophotometer. Along with controls and samples, protein carbonyl standards were also included in the assay. The content of the carbonyl protein in the mitochondrial samples was determined as pmol/mg protein, using the standard curve.

Lipid Peroxidation Assay (TBARS):

Lipid peroxidation was quantified by determining 2-thiobarbituric acid reactive substance (TBARS) formation according to the method described by Buege and Aust [*Methods in Enzymol.* 52, 302-310, 1978] with some modification. H1299 cells ($2\times10^{-4}$ cells) were homogenized 1 ml of PBS. 1 ml of 2-thiobarbituric acid (TBA) reagent consisting of 0.375% TBA, 15% trichloroacetic acid, and 0.25 N HCl was added to 0.5 ml of cell homogenate. The mixture of cell suspension and TBA reagent was heated at 100° C. for 20 minutes, chilled quickly in ice-water to room temperature, and centrifuged at 1,500 g for 10 minutes. The supernatant was measured at 535 nm with a spectrophotometer. Statistical analysis:

Results for statistical analysis were obtained from the control subgroup (H1299 cells in medium) and from the various treatment subgroups (with/without saliva and/or exposure to CS and/or treatment with diazepam or clonazepam)

Means, SDs and SEMs were computed and results between the subgroups were analyzed and compared via one-way analysis-of-variance [Scheffe, H. *The Analysis of Variance.* New York: John Wiley & Sons. 1959] using the Bonferroni Multiple-Comparison Test Model [Hockberg and Tamhane, *Multiple Comparison Procedures.* New York: John Wiley & Sons. 1987] to determine significant differences between computed means. The means between each pair of means was analyzed via T-test For Paired Differences and means between each two subgroups were compared via Two Sample T-test For Differences in Means [*Gosset Biometrika* 1908; 6:1-25].

Results are expressed as the mean±standard error $$\{SD/\sqrt{N}\}.$$

Experimental and control groups were usually at n≥5, unless otherwise indicated.

Experimental Results

Figure 4A:
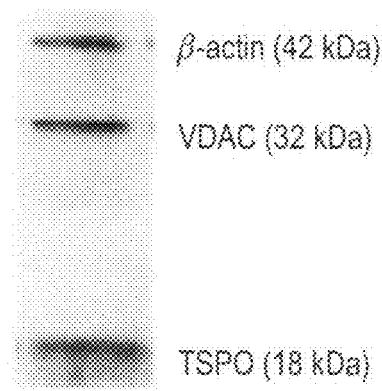
FIGS. 4(A-C) present a Western blot analysis showing the presence of TSPO in human saliva (FIG. 4A), a representative saturation curve (FIG. 4B) and a Scatchard plot analysis (FIG. 4C) of the binding of the synthetic TSPO receptor ligand [$^3$H]PK11195 to TSPO receptors in human saliva. Crude lysates from saliva were prepared, loaded onto the 12% SDS-polyacrylamide gel and transferred onto nitrocellulose membranes with anti-TSPO serum and anti-VDAC for assessment of protein levels, followed by anti-β actin to access and compare the total protein input in each lane (FIG. 4A). Binding assays contained protein extract in the absence (total binding) or presence (nonspecific binding) of 1 μM unlabeled PK 11195. The maximal number of binding sites (Bmax) and equilibrium dissociation constants were calculated from the saturation curve of [$^3$H]PK11195 binding, using Scatchard analysis (FIG. 4C). [$^3$H]PK 11195 was found to bind with high affinity to TSPO receptors in human saliva, yielding Bmax and Kd values of 6,471±1,584 fmol/mg protein and 6.2±1.4 nM, respectively (n=10).

Binding of [$^3$H]PK11195 to the TSPO Receptor in Saliva:

The monomeric TSPO (18 kDa) and its associated protein, VDAC, were detected in human saliva, by western blot analysis (see, FIG. 4A).

Figure 4B:
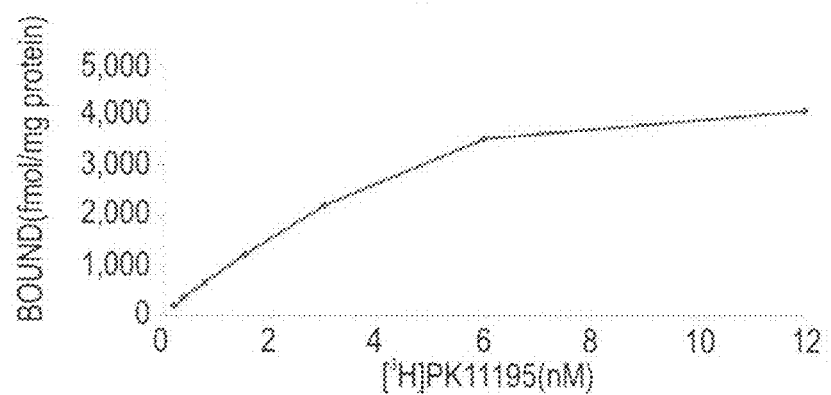
Figure 4C:
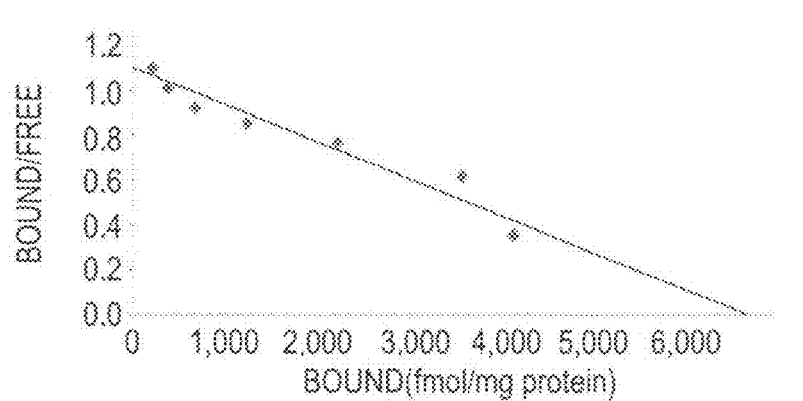

For determination of the salivary TSPO binding characteristics, binding analysis with the TSPO receptor [$^3$H]PK 11195 ligand was performed. Saturation curves of [$^3$H] PK11195 (final concentration: 0.1-12 nM) showed saturable binding characteristics. The mean maximal binding capacity (Bmax) and equilibrium dissociation constant (Kd) values were calculated from the saturation curves with the application of Scatchard analysis to six independent experiments. [$^3$H]PK11195 was found to bind with high affinity to the TSPO receptor in human saliva, yielding Bmax and Kd values of 6,471±1,584 fmol/mg protein and 6.2±1.4 nM, respectively (n=10). A representative Saturation curve for [$^3$H]PK11195 binding, and the corresponding Scatchard analysis in human saliva are presented in FIGS. 4B and 4C, respectively.

These results show that the TSPO receptor is expressed in human saliva and binds PK11195 with high affinity.

Determination of Ki Values for TSPO Ligands:

In order to determine the affinity of various compounds to the human salivary TSPO, competition studies were performed, using five different TSPO receptor ligands (PK11195, FGIN-1-27, Ro5-4864, diazepam and clonazepam). Inhibition of [$^3$H]PK11195 binding to the TSPO by the various compounds was examined in four independent experiments, in the presence of various (six) concentrations of the compounds. Ki values (concentration causing 50% inhibition of [$^3$H]PK11195 binding) were derived from such competition studies and are presented in Table 1.

The PK11195 binding affinity was found to be two orders of magnitude higher than that of Ro5 4864. The binding affinity of PK11195 was two orders of magnitude higher than that of FGIN-1-27, and three orders of magnitude higher than that of diazepam. As expected, the CBR specific ligand, clonazepam, exhibited negligible affinity to TSPO.

TABLE 1

| Compound | Ki (nM) |
|---|---|
| PK 11195 | 6 |
| FGIN-1-27 | 150 |
| Ro5-4864 | 500 |
| Diazepam | 4500 |
| Clonazepam | >10000 |

The Effect of CS on the Binding Capacity of Salivary TSPO In Vitro:

Saliva samples were exposed to CS for various time lengths ranging from 5 to 90 minutes, with a pressure of 0.2 bar. Although no difference in the PK11195 binding affinity to TSPO receptor was detected after 5-30 minutes of exposure to CS, after an exposure time length of 45-90 minutes a significant reduction of 25±5% in binding affinity was detected as compared to control saliva, not exposed to CS (n=3).

Figure 5:
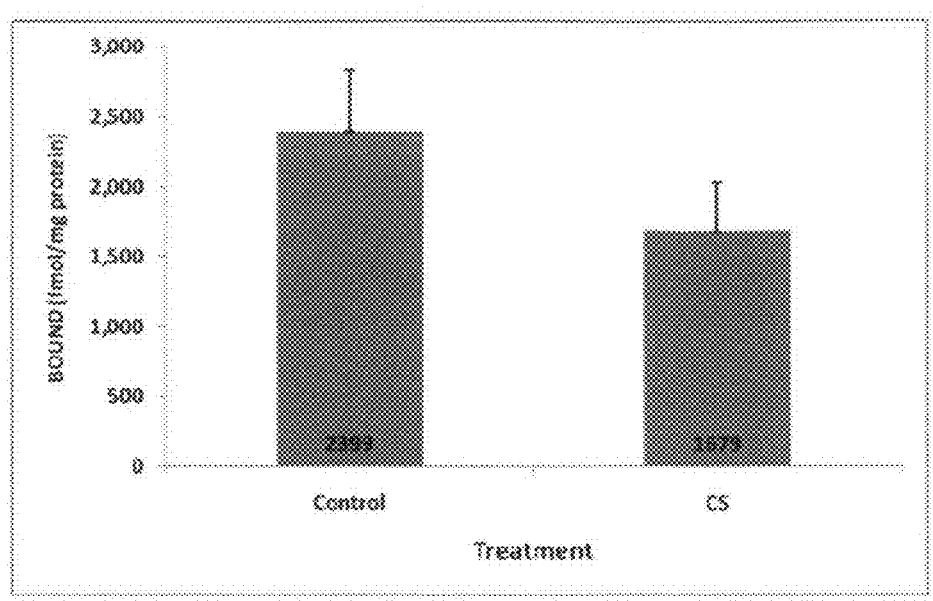
FIG. 5 presents a bar graph depicting the effect CS on the binding of the synthetic TSPO receptor ligand [$^3$H]PK11195 to TSPO receptors in saliva exposed to CS for 60 minutes (CS) as compared to non-exposed saliva (control). Binding assays contained protein extract in the absence (total binding) or presence (non-specific binding) of 1 μM unlabeled PK 11195.

After 60 minutes, B values for TSPO receptor binding were significantly reduced, by 30%, in saliva exposed to CS as compared to control. (n=34, p<0.01; see, FIG. 5). Cell-viability assays showed no change in the percentage of viable cells following 45-90 minutes exposure to CS, as compared to control samples.

Thus, these results show a CS-dependent decrease in TSPO receptor binding capacity which is not via a mechanism of cell death.

Figure 6A:
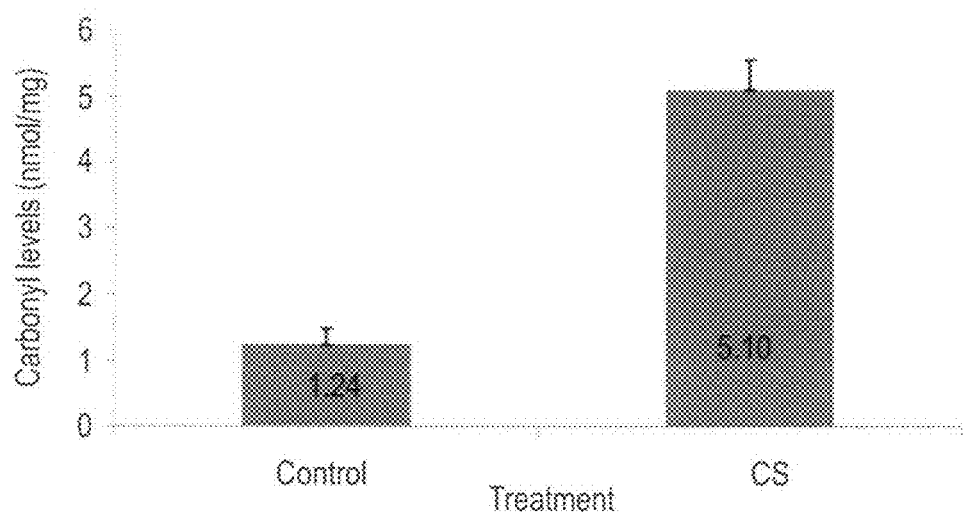
FIGS. 6(A-B) are bar graphs showing the effect CS on protein carbonylation (FIG. 6A) and level of lipid peroxides, as indicated by the percentage of the absorbency values (FIG. 6B) in saliva, as compared to control. The lipid oxidation products (lipid peroxides) were measured calorimetrically using the TBARS assay. The results are expressed as mean values±SE.

Detection of CS-Induced Oxidative Stress in Saliva:

For evaluation of the oxidative stress induced to the salivary cells by CS, two well-established methods for detection of oxidation of proteins and lipids were used as follows:

Detection of Protein Oxidation (the Protein Carbonyl Assay):

Saliva samples were collected from healthy non-smoking volunteers, exposed to CS in-vitro, and used for quantitative analysis of protein oxidation. This analysis was performed by the Protein Carbonyl assay, using a commercial kit. The mean levels of protein oxidation products (carbonyls) in control and CS-exposed saliva, as calculated from seven different saliva samples, are presented in FIG. 6A. A significant four-fold increase in the carbonyl levels was observed in CS-exposed samples, as compared to control saliva (p<0.01). This finding indicates that CS induces oxidative injury to the salivary cells, resulting in a four-fold increase in the protein oxidation rate.

Detection of Lipid Oxidation (the TBARS Assay):

Saliva samples were collected from healthy non-smoking volunteers, exposed to CS in-vitro and subjected to lipid oxidation analysis. The lipid oxidation products (lipid peroxides) were measured calorimetrically using the TBARS assay, and the ratio between the absorbency values of control and CS-exposed saliva was calculated.

Figure 6B:
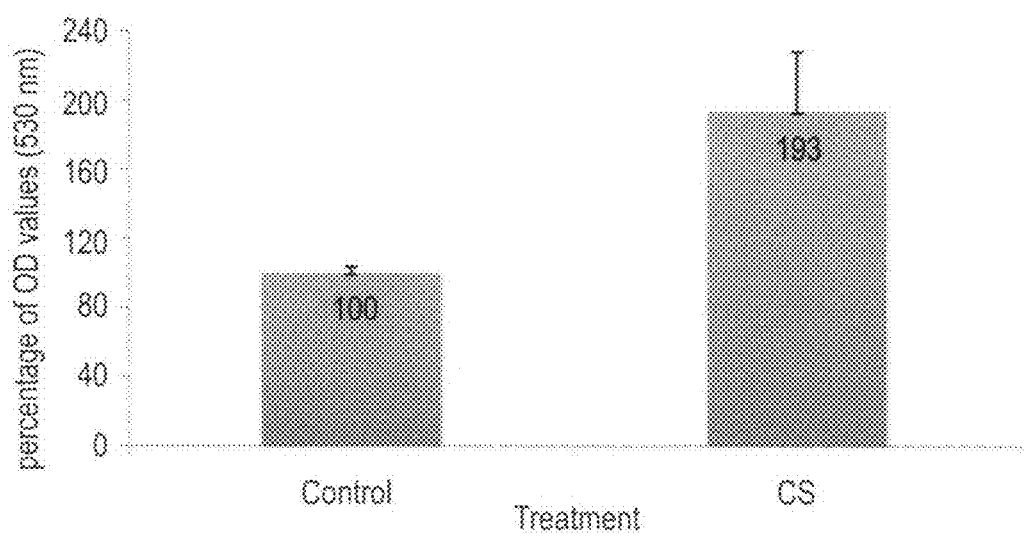

FIG. 6B presents the mean percentage of absorbency values, indicating the mean percentage of lipid peroxides. These values were calculated from three independent experiments, using eleven different saliva samples. An approximately two-fold increase in the lipid peroxides was observed in CS-exposed samples, as compared to control saliva. The increase was found to be statistically significant ($p<0.01$).

Taken together the two tests, for oxidative damage, show that CS induces oxidative injury to the salivary cells.

Effects of Antioxidants of Binding Capacity of TSPO:

One way to assay whether the effect of CS on the TSPO binding is mediated via oxidants is by preventing (or partially preventing) this effect by means of antioxidants. The ability of four different antioxidants to prevent the CS effect on the TSPO was evaluated. The following anti-oxidative compounds were tested: Penicillamine (1 mM and 5 mM), Hydroxocobalamine (1 mM), Desferal (5 mM), and Glutathione (2 mM). The compounds were added separately to the saliva samples several minutes prior to their exposure to CS. Saliva samples that were not incubated with antioxidants were used for standardization.

The results showed similar enhanced binding in both control samples and CS-exposed samples, as compared to the standard samples. Thus, reactive oxygen species (ROS) and aldehydes in cigarette smoke (CS) do not appear to be responsible for the CS-related inhibition of TSPO receptor binding capacity in saliva.

Exposure of Human Saliva to Cigarette Smoke (CS), In-Vivo Experiments:

The effect of long term CS-exposure on the salivary TSPO, of heavy smokers, was investigated. Saliva samples were collected from heavy smokers (smokers group) and from a control group of non-smoking volunteers (control group), and the total protein expression level as well as TSPO binding capacity was evaluated as follows.

Figure 7A:
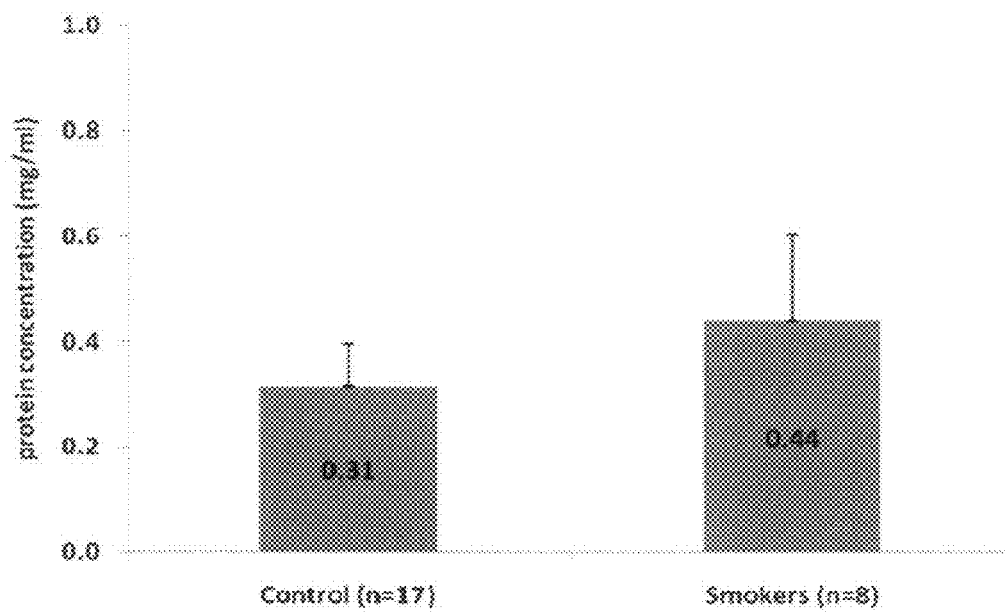
FIG. 7(A-B) are bar graphs showing the similar total protein levels (FIG. 7A) yet reduced binding of [$^3$H]PK11195 to TSPO receptors (FIG. 7B) in saliva cells from smokers as compared to non-smokers (control). The total protein concentration was quantified using the Bradford method. The results are expressed as mean values±SE.

Total Protein Concentration in Saliva Cells from Heavy Smokers:

The total protein expression level of saliva cells from heavy smokers as compared to non-smokers was examined. Protein levels were quantified, using the Bradford method [Bradford M. M. 1976. *Anal. Biochem.* 72:248-254]. The results, as calculated from three independent assays, showed similar total protein concentration in the two groups (FIG. 7A). According to these findings, long-term exposure of saliva to CS does not induce significant changes in the saliva total protein levels.

Figure 7B:
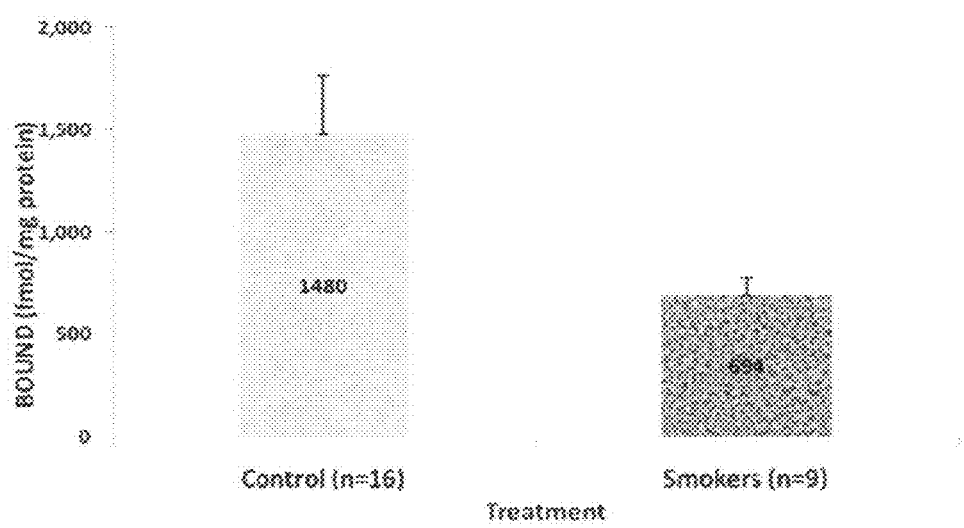

TSPO Receptor Binding Capacity in Saliva from Heavy Smokers:

Three independent binding assays of [$^3$H]PK11195 ligand (final concentration 6 nM) to the TSPO receptor were performed, in saliva samples of both groups. The mean TSPO binding was calculated and found to be 53% lower in the smokers group, as compared to the control group (694±264; n=9 and 1,480±1,157; n=16, respectively; see, FIG. 7b). This statistically significant reduction ($p<0.05$) further supports the results obtained for the in-vitro exposure of saliva cells to CS (detailed above), and point to a CS-related reduced TSPO receptor binding capacity.

Figure 8B:
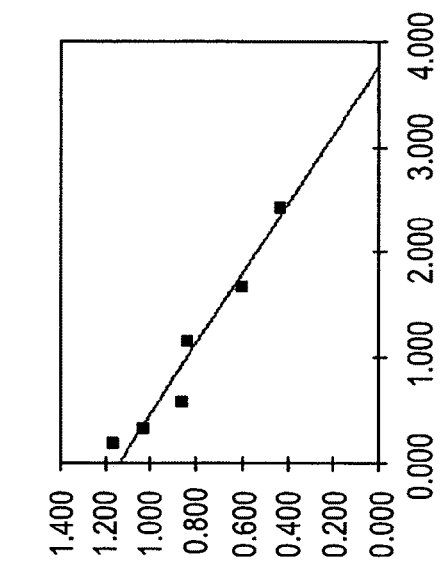
FIGS. 8(A-D) present Scatchard plot analyses of the binding of the synthetic TSPO receptor ligand [$^3$H]PK11195 to TSPO receptors in human tongue cancer cell lines SCC-25 and SCC-15. Shown are saturation curves (FIGS. 8A and 8C) and Scatchard plots (FIGS. 8B, and 8D) for SCC-25 and SCC-15, respectively. The calculated (Bmax) and Kd values for the [$^3$H]PK11195 binding to TSPO receptors were 3133±643 fmoles/mg protein and 5.75±2.0 nM respectively for SCC-25 and 6956±5492 fmoles/mg protein and 5.95±4.6 nM respectively for SCC-15.
Figure 8D:
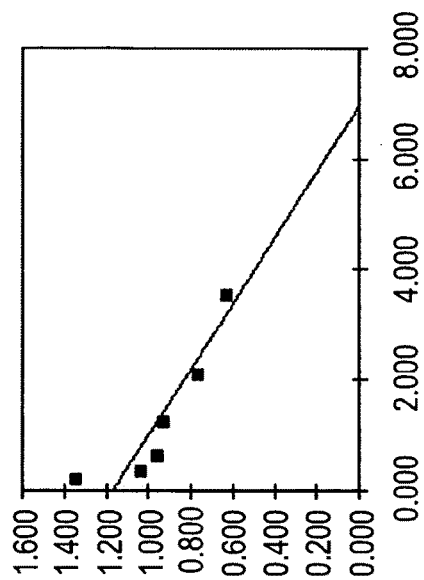
Figure 8A:
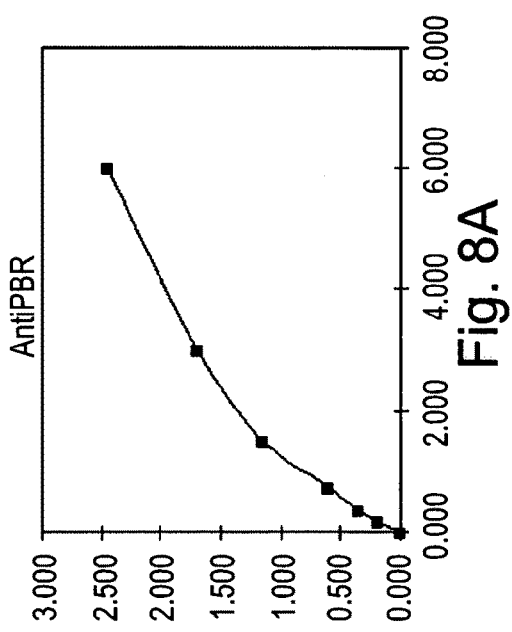
Figure 8C:
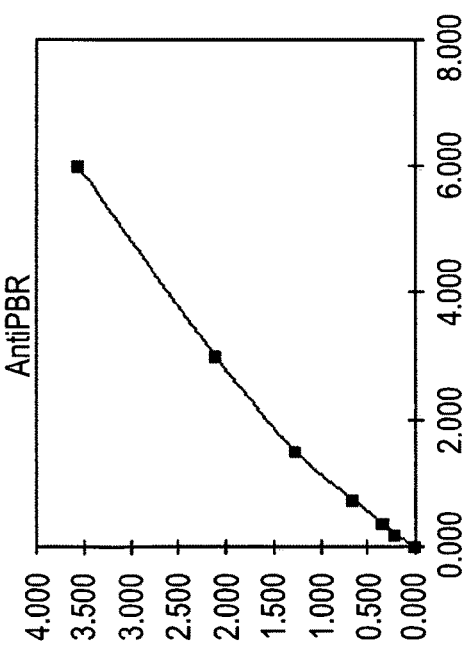

Binding Characteristics of [$^3$H]PK11195 to SCC-25 and SCC-15 Cell Lines:

Scatchard analysis of [$^3$H]PK11195 specific binding to human tongue cancer cell lines SCC-25 and SCC-15 was performed (see, FIGS. 8A and 8C for saturation curves, and FIGS. 8B and 8D for Scatchard plots for SCC-25 and SCC-15, respectively). [$^3$H]PK11195 (0.19-6 nM final concentration) bound with high affinity to the human tongue cancer cell line-SCC-25, yielding maximal binding capacity (Bmax) and equilibrium dissociation constant (Kd) values of 3133±643 fmoles/mg protein and 5.75±2.0 nM respectively.

Non-specific binding of [$^3$H]PK11195 to SCC-25 was a third of the total binding. Similar results were obtained for the binding of [$^3$H]PK 11195 (0.19-6 nM final concentration) to TSPO receptor in SCC-15 cells, with a Bmax and Kd values of 6956±5492 fmoles/mg protein and 5.95±4.6 nM respectively. Non-specific binding of [$^3$H]PK11195 to SCC-15 cells was a fourth (25±3.2%) of the total binding.

$IC_{50}$ Values for TSPO Receptor Ligands in SCC-25 and SCC-15 Cell Lines:

A series of competition studies using 5 compounds were conducted in order to determine the $IC_{50}$ of various compounds in displacing of [$^3$H]PK11195 from TSPO receptors in SCC-25 and SCC-15 cell lines. $IC_{50}$ values (concentration causing 50% inhibition of [$^3$H]PK11195 binding) were derived from such competition studies and are presented in Table 2 and Table 3 for SCC-25 and SCC-15, respectively.

The potency of the PK11195 in displacing [$^3$H]PK11195 from SCC-25 membrane is 17 times higher than FGIN-1-27. The potencies of Ro5 4864 and diazepam in displacing [$^3$H]PK11195 are 74 and 1580 lower than PK 11195, respectively. Clonazepam, a CBR specific ligand, exhibited negligible affinity for TSPO.

TABLE 2

| Compound | $IC_{50}$ (nM) |
|---|---|
| PK 11195 | 9 ± 3 |
| FGIN-1-27 | 152 ± 19 |
| Ro 5-4864 | 666 ± 36 |
| Diazepam | 14242 ± 5720 |
| Clonazepam | >100,000 |

TABLE 3

| Compound | $IC_{50}$ (nM) |
|---|---|
| Clonazepam | >100,000 |
| PK 11195 | 6 ± 5 |
| FGIN-1-27 | 164 ± |
| Ro 5-4864 | 2073 ± 1547 |
| Diazepam | 14125 ± 15155 |

Detection of TSPO Receptor and VDAC in SCC-25 and SCC-15 Cells:

The monomeric TSPO (18 kDa) and its associated protein, VDAC, were detected in SCC-25 and SCC-15 cell lines, by Western blot analysis (see, FIGS. 9A and 9B respectively).

Detection of CS-Induced Oxidative Stress in SCC-25 and SCC-15 Cells:

Active and passive smokers are exposed to reactive free radicals present in CS. Free radicals and reactive nitrogen species originating from CS are frequently considered to be the reagents capable of triggering processes leading to malignant transformation.

For evaluation of the oxidative stress induced to SCC-25 and SCC-15 cells by CS, the Protein carbonyl assay, for detection of protein oxidation, was used. The mean levels of protein oxidation products (carbonyls) in control and CS-exposed SCC-25 and SCC-15 cells, are presented in FIGS. 9C and 9D, respectively. A significant six-fold increase in the carbonyl levels was observed in CS-exposed cells, as compared to control cells. This finding indicates that CS induces oxidative injury to human tongue cancer cell lines, results in a significant, substantial increase in the protein oxidation rate.

Figure 10A:
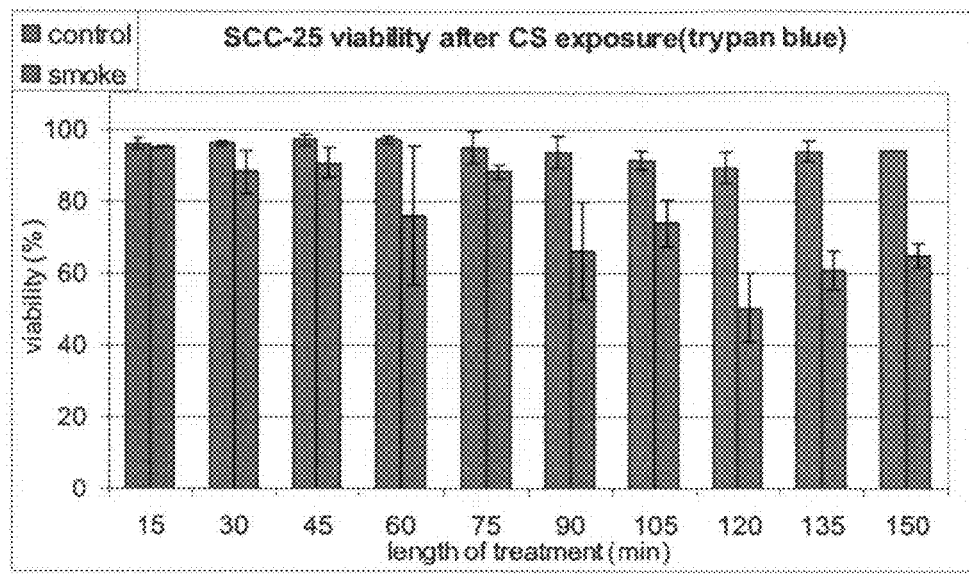
FIGS. 10(A-B) present bar graphs showing the CS-induced decrease in SCC-25 (FIG. 10A) and SCC-15 (FIG. 10B) cell viability. Viability of cells was assessed using the Trypan blue exclusion test. Cells were stained with the vital dye Trypan Blue at final concentration of 0.25% and placed on a hemocytometer. Visual counting was preformed by inverted microscope.
Figure 10B:
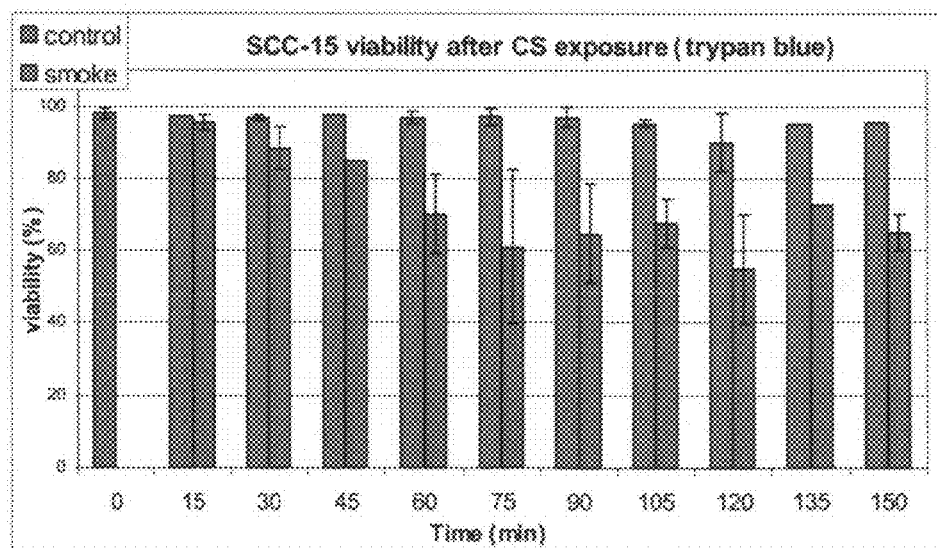

SCC-25 and SCC-15 Cell Viability Following Exposure to CS:

The viability of SCC-25 and SCC-15 cells following exposure to CS for various length of time was measured, using the Trypan blue exclusion method, and compared to viability of control cells not exposed to CS. Although, a time-dependent decrease in cell viability was observed both for CS-exposed cells and for control, the decrease was significantly larger in cells exposed to CS for more than 45 minutes (see, FIGS. 10A and 10B for SCC-25 and SCC-15 respectively; $p<0.01$).

Figure 11A:
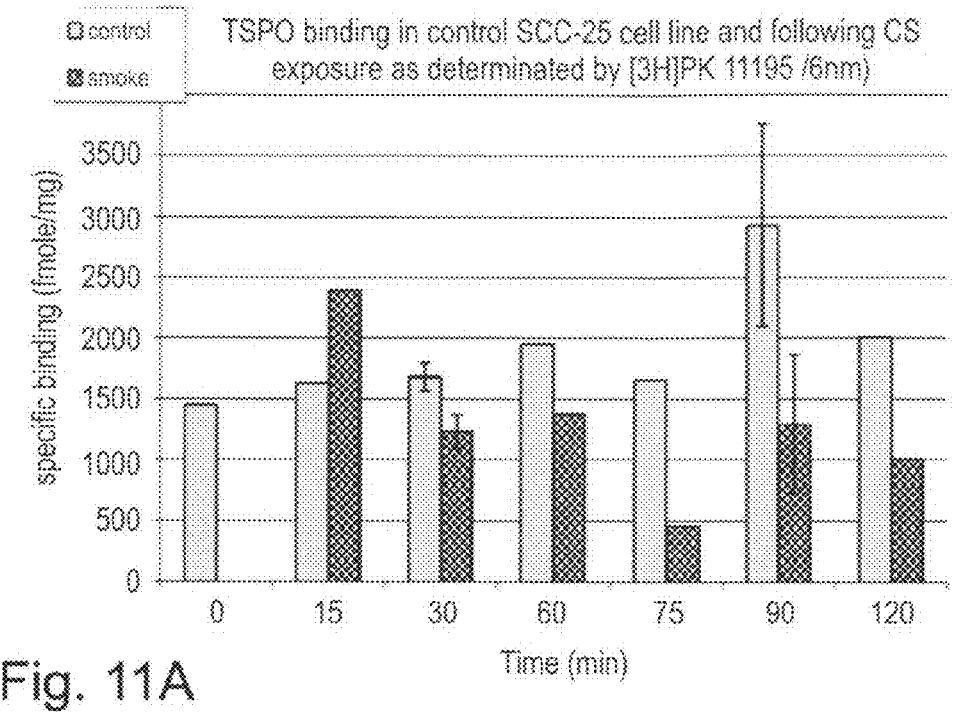
FIGS. 11(A-B) present bar graphs depicting the effect of CS on the specific binding of the TSPO receptor ligand [$^3$H]PK11195 to the TSPO receptors in SCC-25 (FIG. 11A) and SCC-15 (FIG. 11B) cell lines at various time lengths of CS exposure. The results show a significant decrease in [$^3$H]PK 11195 binding affinity, in cells exposed to CS for more than 30 minutes as compared to control cells (n=2; p<0.05).
Figure 11B:
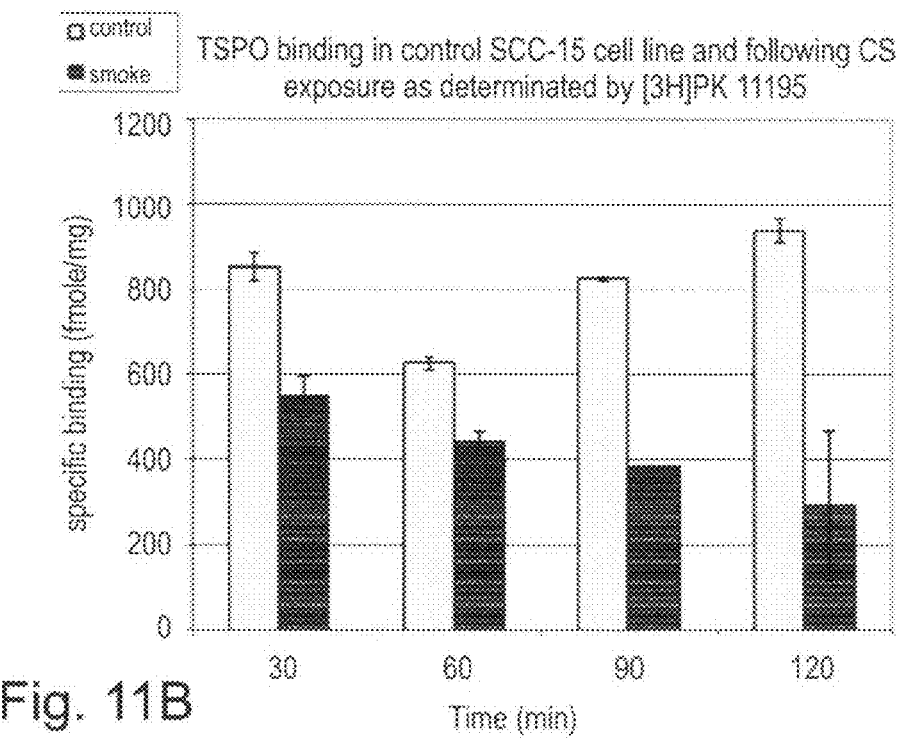

Effect of CS on TSPO Receptor Binding Capacity in SCC-25 and SCC-15 Cell Lines:

Scatchard analysis of [$^3$H]PK11195 specific binding to human tongue cancer cell lines SCC-25 and SCC-15 exposed to CS was performed and compared to non-exposed control cell. Shown in FIGS. 11A and 11B are the specific binding affinities of [$^3$H]PK11195 to TSPO receptor in SCC-25 and SCC-15 cells respectively. The results show a significant decrease in [$^3$H]PK11195 binding affinity, in cells exposed to CS for more than 30 minutes as compared to control cells ($p<0.05$). The decrease is proportional to the CS-exposure time. Short CS-exposures (less than 30 minutes) caused insignificant increases in [$^3$H]PK 11195 binding.

Figure 12A:
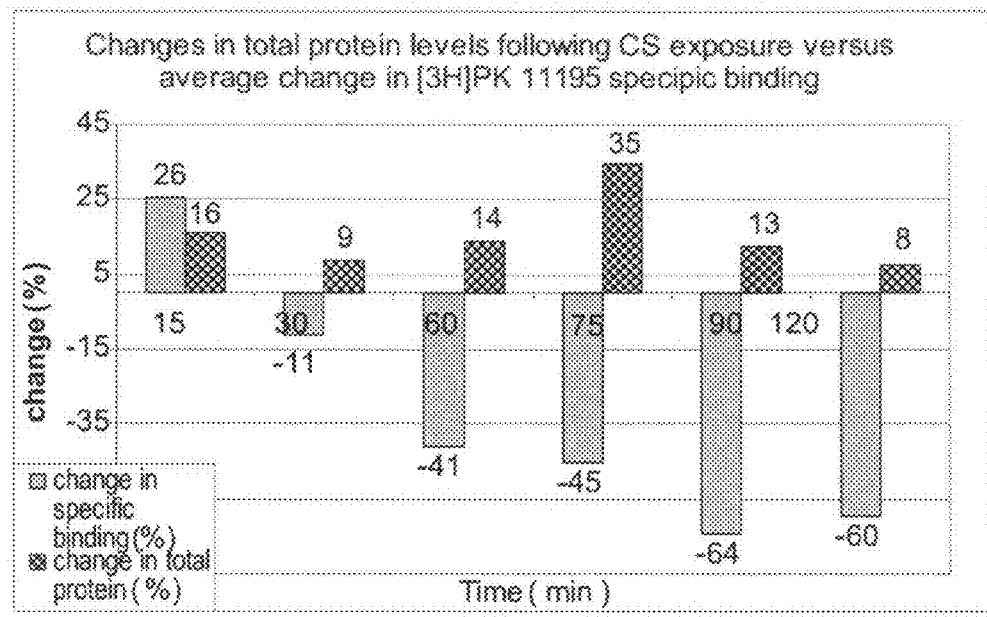
FIGS. 12(A-D) present bar graphs showing a CS-dependent increase in total protein levels, yet a decrease in specific binding of $^3$H]PK11195 to the TSPO receptors, in SCC-25 cells (FIG. 12A) and in SCC-15 cells (FIG. 12B) and Western blot analyses showing an increase in protein level of TSPO receptor and VDAC, following CS exposure (FIGS. 12C and 12D for SCC-25 cells and SCC-15 cells, respectively). Total protein levels were measured using the Bradford method. For evaluation of TSPO and VDAC levels, crude lysates of SCC-25 cells and SCC-15 cells, exposed to CS for various time lengths, were prepared, loaded onto gradient SDS gels, transferred to nitrocellulose and blotted with anti-TSPO serum and anti-VDAC followed by anti-β actin to access and compare the total protein input in each lane.
Figure 12B:
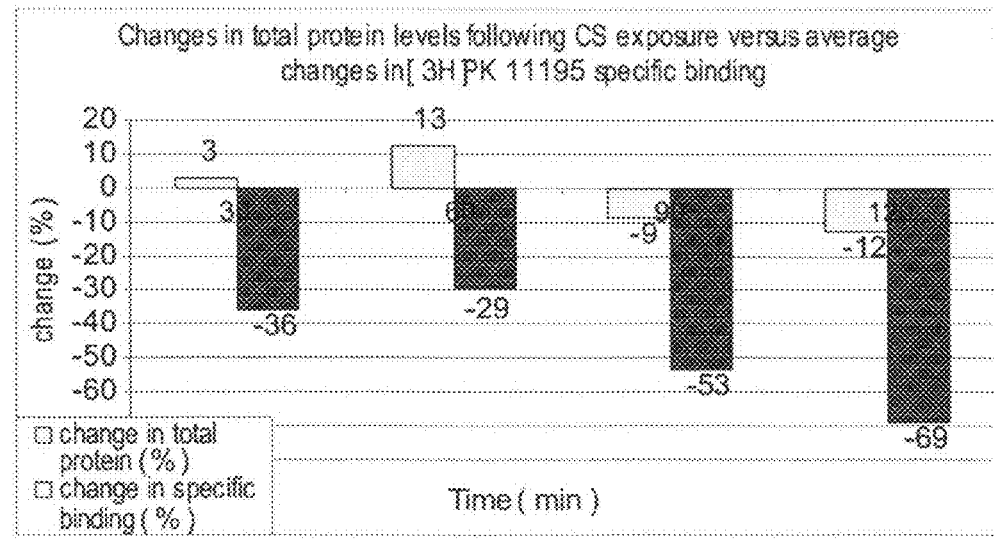

In order to test whether the decreased binding affinity of the TSPO receptor ligand [$^3$H]PK11195 to the TSPO receptors is due to altered protein expression levels, the level of total protein in SCC-25 and SCC-15 cells exposed to CS as compared to control cells was measured using the Bradford method. The obtained results showed an increase rather than a decrease in total protein levels of cells exposed to CS (see FIGS. 12A and 12B for SCC-25 and SCC-15, respectively). Thus, the CS-dependent decrease in TSPO receptor binding capacity is not due to a CS-dependent decrease in protein expression levels.

Measurements of TSPO Protein Levels in SCC-25 and SCC-15 Cells Exposed to CS:

The effect of CS on TSPO and VDAC accumulation was tested and analyzed. SCC-25 and SCC-15 cells were exposed, for time lengths of 30-180 minutes, to CS. Western blot analysis was performed and the amount of TSPO and VDAC was evaluated.

In SCC-25 cell line, short exposure of cells to CS (less than 30 minutes) caused a decrease in the protein level of the TSPO receptor and of VDAC (see, FIG. 12C). An opposite, increase in protein levels was detected in longer exposure times (more than 30 minutes).

In SCC-15 cell line an increase in protein levels of TSPO receptor and VDAC was detected in cells exposed to CS, in all time length (see FIG. 12D).

Figure 13A:
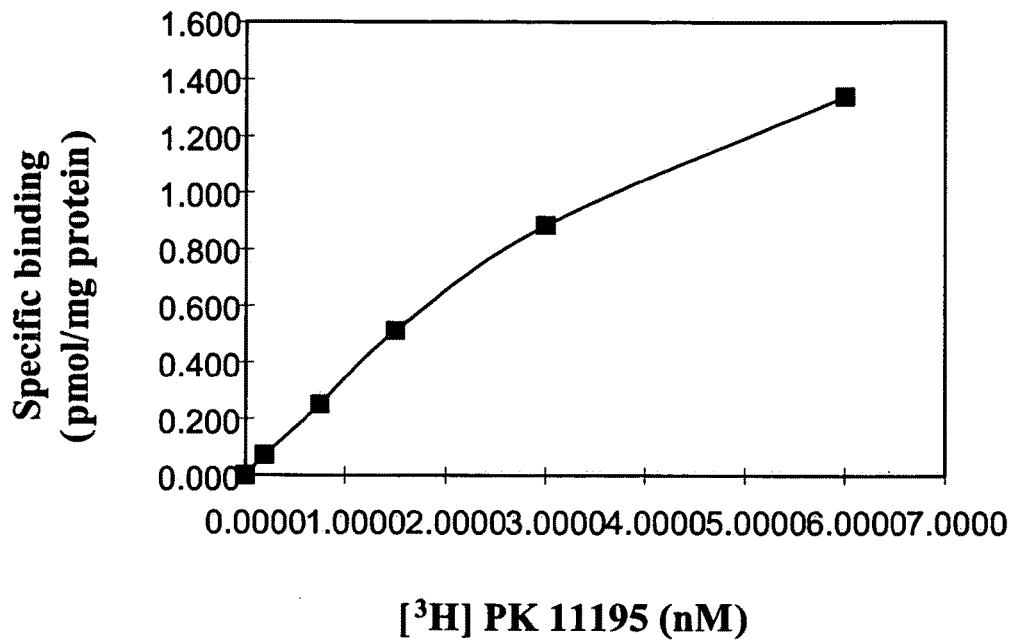
FIG. 13 presents Scatchard plot analysis of the binding of the synthetic TSPO receptor ligand [$^3$H]PK11195 to TSPO receptors in H1299 cells. The maximal number of binding sites (Bmax) and equilibrium dissociation constants were calculated from the saturation curve of [$^3$H]PK11195 binding, using Scatchard analysis. The Scatchard analysis of the saturation data yielded a straight-line plot (R=0.9). The average Kd value for [$^3$H]PK11195 was calculated to be 9.2±1.3 μM, and the maximum amount of specifically bound ligand (Bmax) was 3274±787 pmol/mg of protein. B; bound. B/F; bound/free. R=0/9, data are from a single experiment carried out in duplicate.
Figure 13B:
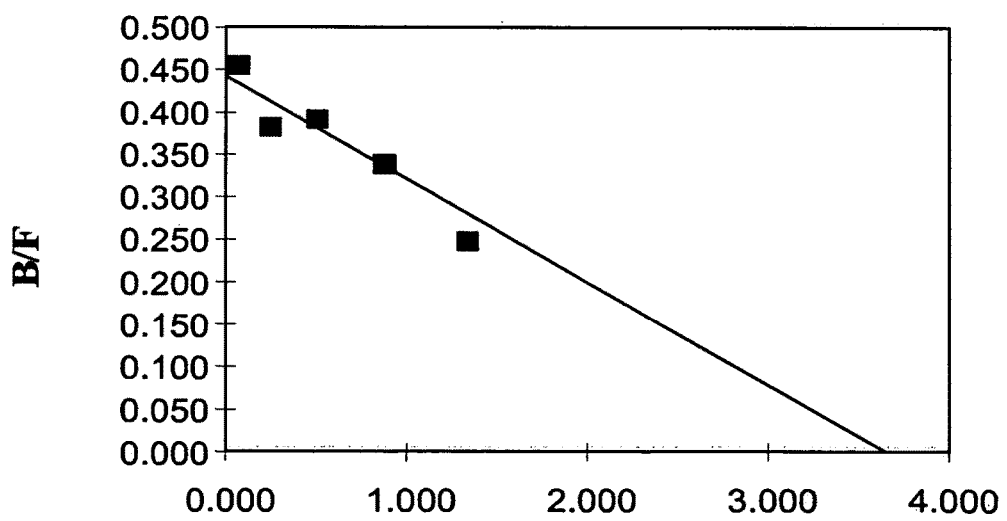

Binding of [$^3$H]PK11195 to the TSPO Receptor in H1299 Lung Cancer Cells Exposed to CS:

In order to investigate the effect of CS on the activity of the TSPO receptor, the binding affinity of the TSPO receptor ligand [$^3$H]PK11195 to the TSPO receptor was tested, in the presence of CS as compared to control. First, the binding of [$^3$H]PK11195 to H1299 lung cancer cells was evaluated using a radiology binding assay. As shown in FIG. 13, Scatchard analysis of the saturation data yielded a straight-line plot ($R=0.9$) with an average Kd value for [$^3$H]PK11195 of $9.2\pm1.3$ µM, and a calculated maximum amount of specifically bound ligand (Bmax) of $3274\pm787$ pmol/mg of protein. These results show that, in H1299 lung cancer cells, [$^3$H]PK11195 binds with high affinity to TSPO receptors.

Figure 14:
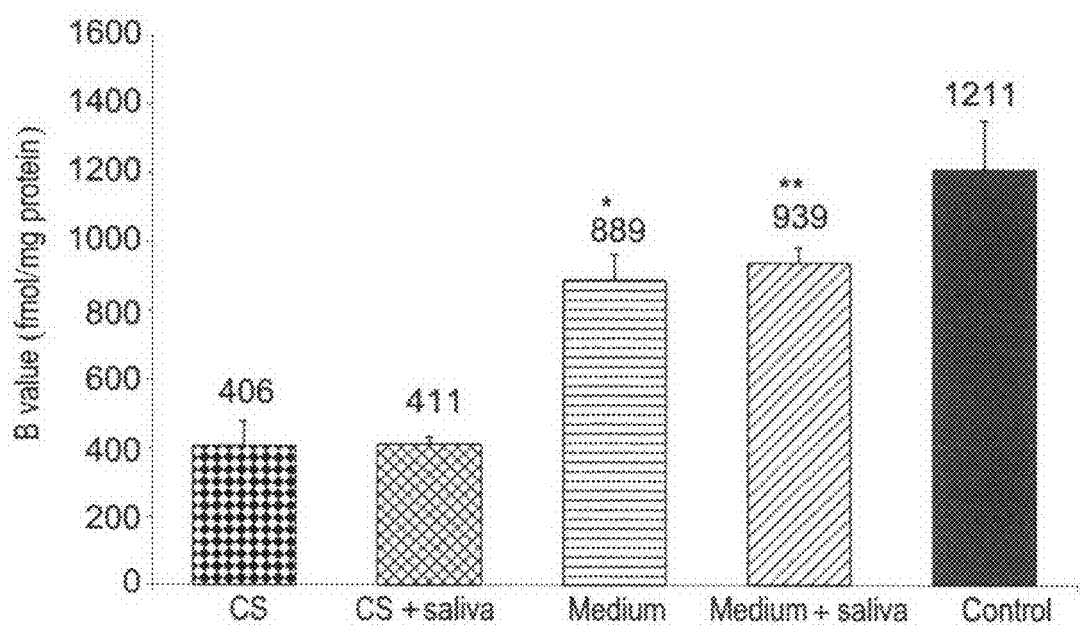
FIG. 14 presents bar graphs depicting the effect of CS on the binding of the TSPO receptor ligand [$^3$H]PK11195 to the TSPO receptors in H1299 cells. TSPO receptor ligand binding assay using [$^3$H]PK11195 was performed on whole cells extracts from cells incubated with medium and exposed to air for 60 minutes (horizontal stripes), medium+30% saliva and exposed to air for 60 minutes (diagonal stripes), medium and exposed to CS for 60 minutes (black diamonds) and medium+30% saliva and exposed to CS for 60 minutes (white diamonds). Whole cells extracts from cells, not incubated or exposed to any factor, served as control (black). Shown in FIG. 5 are the (B) values for the binding of [3H] PK11195 to the TSPO receptor in the various incubation conditions. The results show that the calculated B value for [$^3$H]PK11195 to the TSPO receptor in cells incubated with CS or CS+30% saliva was significantly smaller by 2-folds, as compared to cells not exposed to CS (*,** p<0.005). Results are represented as ±SD (n=3).

The binding of [$^3$H]PK11195 to TSPO receptors in H1299 lung cancer cells exposed to CS or CS and saliva as compared to cells exposed to clear air or clear air+saliva was then tested. The results, presented in FIG. 14, show that the binding of [$^3$H]PK11195 to TSPO receptors is significantly reduced in cells exposed to CS (2 fold decrease in the B value). These results point to a CS-related reduced activity of the TSPO receptor in H1299 lung cancer cells.

Measurements of TSPO Protein Levels in H1299 Cells Exposed to CS:

The effect of CS on TSPO and VDAC accumulation was tested and analyzed. Human lung cancer cells were exposed for 120 minutes to CS with or without the presence of saliva. Western blot analysis was performed and the amount of TSPO and VDAC was evaluated.

Figure 15:
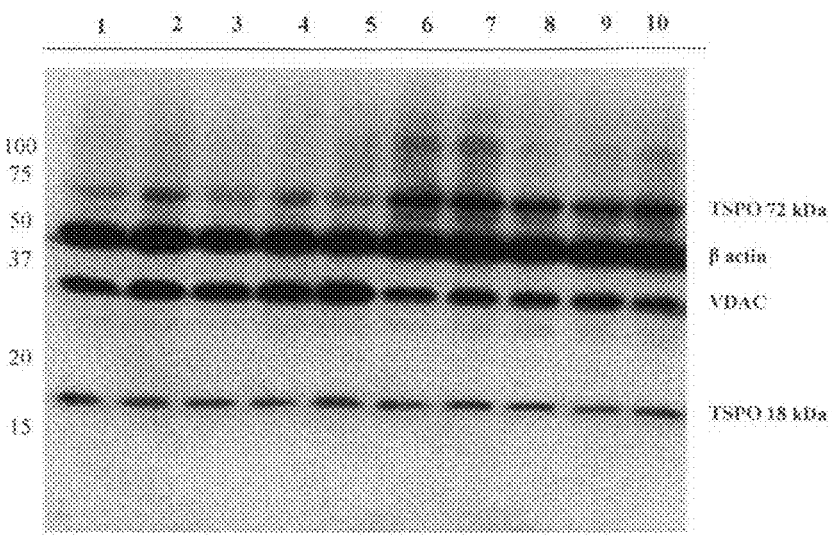
FIG. 15 presents a Western blot analysis showing a reduction in the protein level of TSPO and increase in the protein levels of VDAC, following CS exposure and saliva supplementation. Crude lysates of H1299 human lung cancer cells exposed to CS for 120 minutes and supplemented with saliva in the following combinations: only CS (1) CS+20% saliva (2), CS+25% saliva (3), CS+33% saliva (4), CS+50% saliva (5), only Medium and exposed to air (6), Medium+20% saliva and exposed to air (7), Medium+25% saliva and exposed to air (8), Medium+33% saliva and exposed to air (9) and Medium+50% saliva and exposed to air (10) were prepared, loaded onto gradient SDS gels, transferred to nitrocellulose and blotted with anti-TSPO serum and anti-VDAC followed by anti-β actin to access and compare the total protein input in each lane. It can be clearly seen that the level of the 72 kDa TSPO tetramer (but not the 18 kDa monomer) is decreased and the level of VDAC (which is another known protein of the MPTP complex) is increased in cells exposed to either CS or CS+saliva as compared to the protein level in cells not exposed to CS.

As shown in FIG. 15, exposure to CS or to CS+33% saliva dramatically decreased the level of the 72 kDa TSPO tetramer (but not the 18 kDa monomer) whereas the level of VDAC (which is another known protein of the MPTP complex) was increased.

Figure 16:
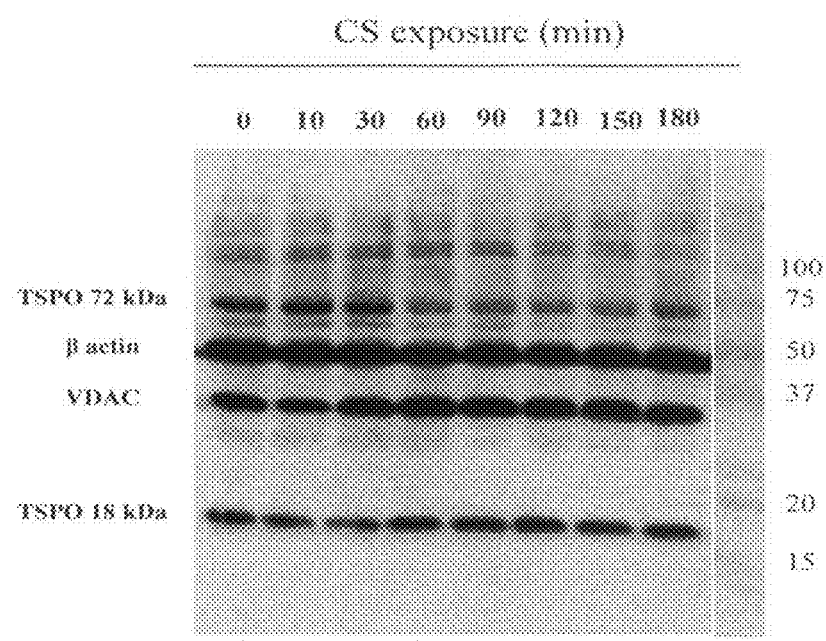
FIG. 16 presents a Western blot analysis showing that the level of TSPO protein in H1299 human lung cancer cells is reversely proportional to the exposure time of the cells to CS. Crude lysates of H1299 human lung cancer cells exposed to CS for various time lengths, were prepared, loaded onto gradient SDS gels, transferred to nitrocellulose and blotted with anti-TSPO serum and anti-VDAC for assessment of protein levels, followed by anti-β actin to access and compare the total protein input in each lane. The results show that the TSPO protein level is reduced in cells exposed to CS in a time dependent manner whereas the protein levels of VDAC reach a maximum level at 30 minutes with no further increase with prolonged exposure time.

As shown in FIG. 16, the decrease in 72 kDa TSPO tetramer protein levels is reversely proportional to the extent of exposure of the cells to CS, whereby longer periods of exposure lead to decreased protein levels. The increase in VDAC protein levels reaches a maximum level after 30 minutes with no further increase with prolonged exposure time.

These results point to a CS-induced alteration/reduction of TSPO receptor levels in H1299 cells, suggesting a decreased TSPO receptor activity in cells of subjects exposed to cigarette smoke.

It has been previously demonstrated that re-organization and polymerization of TSPO could occur following UV photo-irradiation as a ROS source. It has also been suggested that TSPO polymerization by covalent dityrosines bonds is a dynamic process that can modulate TSPO functions, such as steroidogenesis, and that TSPO ligand may bind better to the TSPO polymer than to the monomer form.

The obtained data demonstrate that exposure to CS, as a source of ROS, results in downregulation of TSPO tetramer-complex. Without being bound to any particular theory, it is suggested that the [$^3$H] PK11195 binding decrease following CS exposure may be attributed to the TSPO polymer degradation.

Effect of Diazepam and Clonazepam on Cells Viability:

In order to examine the possible effect of TSPO receptor ligands on the survival rate of cells exposed to both CS and saliva, the benzodiazepine TSPO ligand, diazepam, was added to cells prior to exposing the cells to CS+30% saliva. For comparison, the effect of another benzodiazepine, clonazepam, was also examined. Clonazepam is a benzodiazepine which does not bind to the TSPO receptor (also known as the peripheral benzodiazepine receptor; PBR) but rather only to the central benzodiazepine receptor (CBR).

Figure 17:
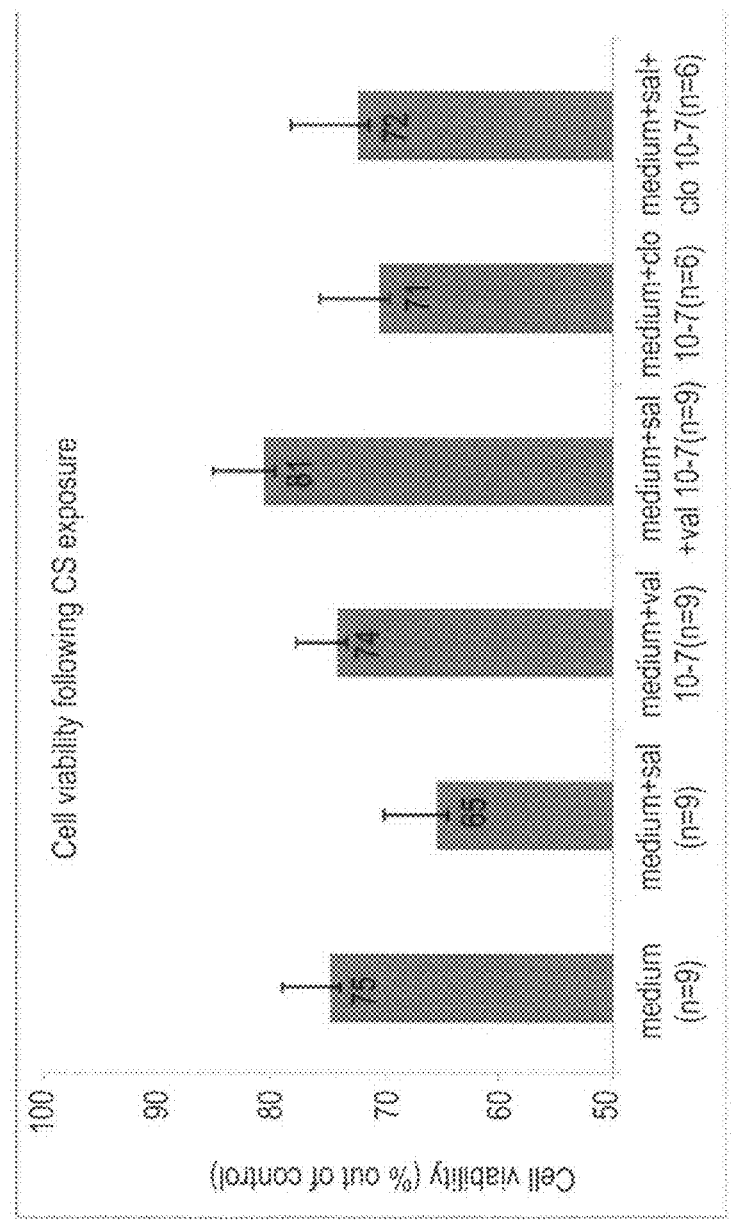
FIG. 17 presents bar graphs depicting the effect of diazepam and clonazepam treatment, at a concentration of $10^{-7}$M, compared to non-treated control, on the survival of H1299 lung cancer cells exposed to CS. Shown in FIG. 8 is the survival level of H1299 lung cancer cells exposed to CS and incubated in the presence of medium, medium+30% saliva (medium+sal) as compared to cells incubated, with medium+$10^{-7}$M diazepam (medium+val), medium+30% saliva+$10^{-7}$M diazepam (medium+sal+val), medium+$10^{-7}$M clonazepam (medium+clo) and medium+30% saliva+$10^{-7}$M clonazepam (medium+sal+clo). The results show that the survival of H1299 lung cancer cells exposed to CS+30% saliva is significantly increased in the presence of $10^{-7}$M diazepam (*p<0.005) and is not significantly altered in the presence of clonazepam.

FIG. 17 presents the percents of viable H1299 cells out of total number of cells upon exposure to CS for 120 minutes and incubation in medium alone or in medium supplemented with 30% (v/v) saliva, with or without prior addition of $10^{-7}$ M diazepam and $10^{-7}$ M clonazepam. These data clearly demonstrate the drastic effect of diazepam on cell survival, with a 16% increase of cell survival in cells incubated in saliva-containing medium and exposed to CS. No significant increase in survival levels could be detected after treatment with Clonazepam.

Figure 18A:
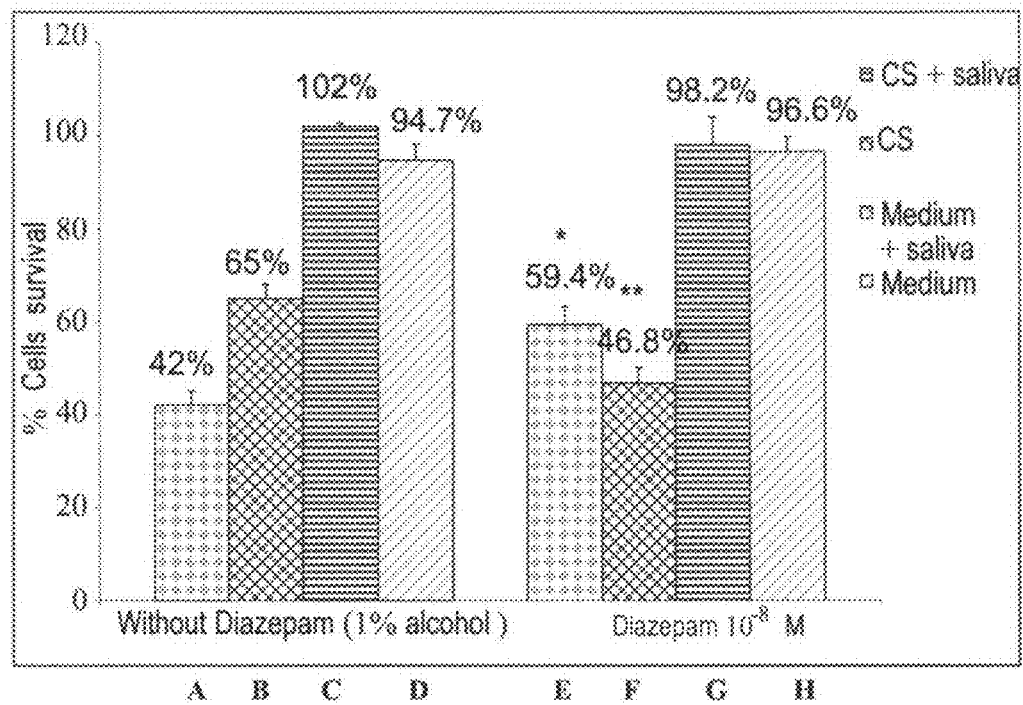
FIGS. 18(A-B) present bar graphs depicting the effect of diazepam (FIG. 18A) and clonazepam (FIG. 18B) treatment, at a concentration of $10^{-8}$M, compared to non-treated control, on the survival of H1299 lung cancer cells exposed to CS. Shown in FIG. 18A is the survival level of H1299 lung cancer cells incubated in the presence of medium+1% alcohol (D) medium+30% saliva+1% alcohol (C) medium+1% alcohol and exposed to CS (B) medium+30% saliva+1% alcohol and exposed to CS (A); as compared to cells incubated, with medium+$10^{-8}$M diazepam (H) medium+30% saliva+$10^{-8}$M diazepam (G) medium+$10^{-8}$M diazepam and exposed to CS (F) medium+30% saliva+$10^{-8}$M diazepam and exposed to CS (E). The results show that the survival of H1299 lung cancer cells exposed to CS+30% saliva is significantly increased in the presence of $10^{-8}$M diazepam (*p<0.005). Shown in FIG. 18B is the survival level of H1299 lung cancer cells incubated in the presence of medium+1% alcohol (D) medium+30% saliva+1% alcohol (C) medium+1% alcohol and exposed to CS (B) medium+30% saliva+1% alcohol and exposed to CS (A); as compared to cells incubated, with medium+$10^{-8}$M clonazepam (H) medium+30% saliva+$10^{-8}$M clonazepam (G) medium+$10^{-8}$M clonazepam and exposed to CS (F) medium+30% saliva+$10^{-8}$M clonazepam and exposed to CS (E). The results show that, clonazepam did not increase the survival level of H1299 lung cancer cells exposed to CS. Cells were incubated with diazepam (n=5) or clonazepam (n=2) prior to the exposure to CS and exposed to CS for 120 minutes (every 20 minutes). The addition of 1% alcohol solvent was used to eliminate artifacts to the results due to a solvent-related effect.
Figure 18B:
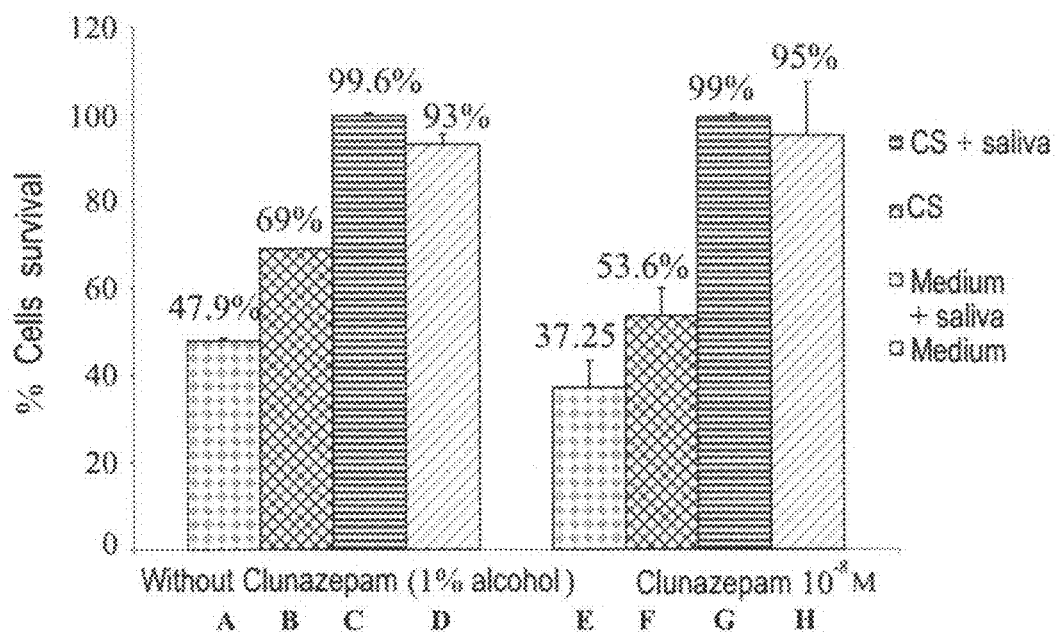

FIG. 18 presents the results obtained with a $10^{-8}$M concentration of diazepam and clonazepam. FIG. 18 shows the percents of viable H1299 cells out of total number of cells upon incubation in medium alone or in medium supplemented with 30% (v/v) saliva, with or without exposure to CS, for 120 minutes and with or without prior addition of $10^{-8}$ M diazepam (see FIG. 9a) and $10^{-8}$ M clonazepam (see FIG. 9b) to the cells incubated with medium+30% saliva and exposed to CS. 1% alcohol was added to control cells (not incubated with diazepam or clonazepam) in order to eliminate artifacts in the results which are related to a solvent-mediated effect. Once again, these data clearly demonstrate the drastic effect of diazepam on cell survival, with a 17.4% increase of cell survival in cells incubated in saliva-containing medium and exposed to CS (p<0.005). Clonazepam exhibits an opposite effect with a 10.65% decrease of cells survival in cells incubated in saliva-containing medium and exposed to CS.

Previous studies have shown that diazepam can modulate antioxidant responses and lower oxidative phenomenon, during short-term administration in subcellular preparations of rat brain regions [Musavi et al. *Mol Cell Biocem* 2000; 206: 97-103]. It has also been shown that a single dose of diazepam can cause free radical mediated changes and that the antioxidant defense response appears to be tissue-region specific [Musavi et al. *Mol Cell Biocem* 1998; 178:41-46]

The above described studies show that the TSPO receptor is substantially affected by CS and that the TSPO ligand diazepam, but not the non-TSPO ligand clonazepam, provides significant protection against cellular loss in the presence of saliva. These results suggest that TSPO receptor ligands, such as diazepam, can be used to protect against tobacco-associated damage.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An article of manufacturing comprising tobacco and a tobacco packaging material, and an agent being incorporated in at least a portion of said tobacco and/or tobacco packaging material, said portion being in contact with an aerodigestive tract of a subject using the article of manufacturing, and said agent being a translocator protein (TSPO) receptor ligand selected from the group consisting of 1-(2-fluoro-5-nitrophenyl)-N-methyl-N-(1-methylpropyl)-3-isoquinolinecarboxyamide (PK11195), (−)-N,N-dimethyl-2-methyl-3-[4-(2-phenyl)quinolinyl]propaneamide (PK14067), (+)-N,N-dimethyl-2-methyl-3-[4-(2-phenyl)quinolinyl]propaneamide (PK 14068), 1-(2-fluoro-5-nitrophenyl)-N-methyl-N-(1-methylpropyl)-3-isoquinolinecarboxyamide (PK 14105), Ro5-6993, Ro5-4864 (4-chlorodiazepam), Ro5-6900, Ro5-6945, Ro5-6669, Ro5-6902, Ro5-6531, Ro5-3448, diazepam, Ro7-5520, Ro5-5115, Ro5-4608, Ro5-6524, Ro5-5122, Ro5-3464, 7-chloro-N,N-5-trimethyl-4-oxo-3-phenyl-3,5-dihydro-4H-pyridazino-[4,5-b]indole-1-acetoamide, SSR180575, DAA1097, DAA1106, and pharmaceutically acceptable salts thereof.

2. An article of manufacturing comprising tobacco and an agent being incorporated in at least a portion of said tobacco, said portion being in contact with an aerodigestive tract of a subject using the article of manufacturing, and said agent being a TSPO receptor ligand selected from the group consisting of 1-(2-fluoro-5-nitrophenyl)-N-methyl-N-(1-methylpropyl)-3-isoquinolinecarboxyamide (PK11195), (−)-N,N-dimethyl-2-methyl-3-[4-(2-phenyl)quinolinyl]propaneamide (PK14067), (+)-N,N-dimethyl-2-methyl-3-[4-(2-phenyl)quinolinyl]propaneamide (PK14068), 1-(2-fluoro-5-nitrophenyl)-N-methyl-N-(1-methylpropyl)-3-isoquinolinecarboxyamide (PK14105), Ro5-6993, Ro5-4864 (4-chlorodiazepam), Ro5-6900, Ro5-6945, Ro5-6669, Ro5-6902, Ro5-6531, Ro5-3448, diazepam, Ro7-5520, Ro5-5115, Ro5-4608, Ro5-6524, Ro5-5122, Ro5-3464, 7-chloro-N,N-5-trimethyl-4-oxo-3-phenyl-3,5-dihydro-4H-pyridazino-[4,5-b]indole-1-acetoamide, SSR180575, DAA1097, DAA1106, and pharmaceutically acceptable salts thereof.

3. An article of manufacturing comprising a tobacco packaging material and an agent being incorporated in at least a portion of said tobacco packaging material, said portion being in contact with an aerodigestive tract of a subject using the article of manufacturing, and said agent being a TSPO receptor ligand selected from the group consisting of 1-(2-fluoro-5-nitrophenyl)-N-methyl-N-(1-methylpropyl)-3-isoquinolinecarboxyamide (PK11195), (−)-N,N-dimethyl-2-methyl-3-[4-(2-phenyl)quinolinyl]propaneamide (PK14067), (+)-N,N-dimethyl-2-methyl-3-[4-(2-phenyl)quinolinyl]propaneamide (PK14068), 1-(2-fluoro-5-nitrophenyl)-N-methyl-N-(1-methylpropyl)-3-isoquinolinecarboxyamide (PK14105), Ro5-6993, Ro5-4864 (4-chlorodiazepam), Ro5-6900, Ro5-6945, Ro5-6669, Ro5-6902, Ro5-6531, Ro5-3448, diazepam, Ro7-5520, Ro5-5115, Ro5-4608, Ro5-6524, Ro5-5122, Ro5-3464, 7-chloro-N,N-5-trimethyl-4-oxo-3-phenyl-3,5-dihydro-4H-pyridazino-[4,5-b]indole-1-acetoamide, SSR180575, DAA1097, DAA1106, and pharmaceutically acceptable salts thereof.

4. The article of manufacturing of claim 1, wherein an amount of said TSPO receptor ligand is such which enables a concentration of said ligand, at the site of the TSPO receptors in a mammalian tissue, to be in the subnanomolar range.

5. The article of manufacturing of claim 1, wherein said TSPO receptor ligand is a benzodiazepine.

6. The article of manufacturing of claim 1, wherein said TSPO receptor ligand is diazepam.

7. The article of manufacturing of claim 1, wherein at least a portion of said tobacco and/or said tobacco packaging material further comprises at least one antioxidant capable of reducing tobacco smoke-associated damage in a subject using the article of manufacturing.

8. The article of manufacturing of claim 1, wherein said tobacco packaging material comprises a filter and said TSPO receptor ligand is impregnated in a paper of said filter.

9. A method of treating a tobacco-associated damage in a subject in need thereof, the method comprising administering to the subject a therapeutically effective amount of a TSPO receptor ligand selected from the group consisting of 1-(2-fluoro-5-nitrophenyl)-N-methyl-N-(1-methylpropyl)-3-isoquinolinecarboxyamide (PK11195), (−)-N,N-dimethyl-2-methyl-3-[4-(2-phenyl)quinolinyl]propaneamide (PK14067), (+)-N,N-dimethyl-2-methyl-3-[4-(2-phenyl)quinolinyl]propaneamide (PK14068), 1-(2-fluoro-5-nitrophenyl)-N-methyl-N-(1-methylpropyl)-3-isoquinolinecarboxyamide (PK14105), Ro5-6993, Ro5-4864 (4-chlorodiazepam), Ro5-6900, Ro5-6945, Ro5-6669, Ro5-6902, Ro5-6531, Ro5-3448, diazepam, Ro7-5520, Ro5-5115, Ro5-4608, Ro5-6524, Ro5-5122, Ro5-3464, 7-chloro-N,N-5-trimethyl-4-oxo-3-phenyl-3,5-dihydro-4H-pyridazino-[4,5-b]indole-1-acetoamide, SSR180575, DAA1097, DAA1106, and pharmaceutically acceptable salts thereof, wherein said therapeutically effective amount is in the subnanomolar range.

10. The method of claim 9, wherein said TSPO ligand is a benzodiazepine.

11. The method of claim 9, wherein said tobacco-associated damage is present in a mucosal tissue.

12. The method of claim 9, wherein said TSPO receptor ligand is used in combination with at least one antioxidant that is capable of reducing a physiological disorder caused by oxidative stress.

13. The article of manufacture of claim 2, wherein an amount of said TSPO receptor ligand is such which enables a concentration of said ligand, at the site of the TSPO receptors in a mammalian tissue, to be in the subnanomolar range.

14. The article of manufacturing of claim 2, wherein said TSPO receptor ligand is a benzodiazepine.

15. The article of manufacturing of claim 2, wherein at least a portion of said tobacco further comprises at least one antioxidant capable of reducing tobacco smoke-associated damage in a subject using the article of manufacturing.

16. The article of manufacturing of claim 3, wherein said tobacco packaging material comprises a filter and said TSPO receptor ligand is impregnated in a paper of said filter.

* * * * *